(12) United States Patent
Arbefeuille et al.

(10) Patent No.: US 11,376,145 B2
(45) Date of Patent: Jul. 5, 2022

(54) DISTAL TORQUE COMPONENT, DELIVERY SYSTEM AND METHOD OF USING SAME

(71) Applicant: Bolton Medical, Inc., Sunrise, FL (US)

(72) Inventors: Samuel Arbefeuille, Sunrise, FL (US); Nico Bahar, Sunrise, FL (US); Eduardo Alejandro Garcia, Sunrise, FL (US); Scott L. Rush, Sunrise, FL (US)

(73) Assignee: Bolton Medical, Inc., Sunrise, FL (US)

( * ) Notice: Subject to any disclaimer, the term of this patent is extended or adjusted under 35 U.S.C. 154(b) by 309 days.

(21) Appl. No.: 16/433,823

(22) Filed: Jun. 6, 2019

(65) Prior Publication Data

US 2019/0321207 A1  Oct. 24, 2019

Related U.S. Application Data

(63) Continuation of application No. PCT/US2018/019510, filed on Feb. 23, 2018.
(Continued)

(51) Int. Cl.
*A61F 2/966* (2013.01)
*A61F 2/07* (2013.01)
*A61F 2/95* (2013.01)

(52) U.S. Cl.
CPC .............. *A61F 2/9662* (2020.05); *A61F 2/07* (2013.01); *A61F 2/9517* (2020.05); *A61F 2002/9665* (2013.01)

(58) Field of Classification Search
CPC ........ A61F 2/9662; A61F 2/07; A61F 2/9517; A61F 2002/9665
See application file for complete search history.

(56) References Cited

U.S. PATENT DOCUMENTS 5,123,917 A  6/1992  Lee
5,242,452 A  9/1993  Inoue
(Continued)

FOREIGN PATENT DOCUMENTS

CN  203815663 U  9/2014
CN  105832447 A  8/2016
(Continued)

OTHER PUBLICATIONS

International Preliminary Report on Patentability for International Application No. PCT/US2018/019510 dated May 5, 2020.
(Continued)

*Primary Examiner* — Richard G Louis
(74) *Attorney, Agent, or Firm* — Foley Hoag LLP

(57) ABSTRACT

A delivery system and method for implanting a stent graft prostheses includes and employs a torque component at a distal end of the stent graft prosthesis, whereby following advancement of the stent graft to a surgical site in a constrained or partially constrained configuration, torque is applied to the torque component and, consequently, to the stent graft to rotationally align the stent graft about a longitudinal axis of the stent graft, followed by deployment of the stent graft in correct rotational alignment, and subsequent retraction of the delivery device from the deployed stent graft and the subject. The torque component includes a pushrod and at least two arms.

28 Claims, 32 Drawing Sheets

Related U.S. Application Data

(60) Provisional application No. 62/579,482, filed on Oct. 31, 2017.

(56) References Cited

U.S. PATENT DOCUMENTS

| | | | |
|---|---|---|---|
| 5,507,769 A | 4/1996 | Marin et al. | |
| 5,755,769 A | 5/1998 | Richard et al. | |
| 5,873,906 A | 2/1999 | Lau et al. | |
| 6,113,623 A | 9/2000 | Sgro | |
| 6,171,334 B1 | 1/2001 | Cox | |
| 6,280,464 B1 | 8/2001 | Hayashi | |
| 6,395,018 B1 | 5/2002 | Castaneda | |
| 6,610,087 B1 | 8/2003 | Zarbatany et al. | |
| 6,776,791 B1 * | 8/2004 | Stallings | A61F 2/95 623/1.11 |
| 7,435,253 B1 | 10/2008 | Hartley et al. | |
| 7,637,940 B2 | 12/2009 | Kocur et al. | |
| 7,763,063 B2 | 7/2010 | Arbefeuille et al. | |
| 8,007,605 B2 | 8/2011 | Arbefeuille et al. | |
| 8,062,346 B2 | 11/2011 | Quigley et al. | |
| 8,128,686 B2 | 3/2012 | Paul, Jr. et al. | |
| 8,172,895 B2 | 5/2012 | Anderson et al. | |
| 8,236,040 B2 | 8/2012 | Mayberry et al. | |
| 8,333,800 B2 | 12/2012 | Bruszewski et al. | |
| 8,480,725 B2 | 7/2013 | Rasmussen et al. | |
| 8,486,129 B2 | 7/2013 | Lautherjung | |
| 8,500,792 B2 | 8/2013 | Berra | |
| 8,641,752 B1 | 2/2014 | Holm et al. | |
| 8,808,351 B2 | 8/2014 | Osborne | |
| 8,915,955 B2 | 12/2014 | West et al. | |
| 8,926,693 B2 | 1/2015 | Duffy et al. | |
| 9,101,455 B2 | 8/2015 | Roeder et al. | |
| 9,101,506 B2 | 8/2015 | Arbefeuille et al. | |
| 9,259,336 B2 | 2/2016 | Schaeffer et al. | |
| 9,364,314 B2 | 6/2016 | Berra et al. | |
| 9,375,308 B2 | 6/2016 | Norris | |
| 9,439,751 B2 | 9/2016 | White et al. | |
| 9,592,112 B2 | 3/2017 | Arbefeuille et al. | |
| 9,827,123 B2 | 11/2017 | Arbefeuille et al. | |
| 9,861,503 B2 | 1/2018 | Barthold et al. | |
| 9,877,857 B2 | 1/2018 | Arbefeuille et al. | |
| 9,913,743 B2 | 3/2018 | Arbefeuille et al. | |
| 10,005,269 B2 | 6/2018 | Hall et al. | |
| 10,080,674 B2 | 9/2018 | Yuan et al. | |
| 10,245,137 B2 | 4/2019 | Scutti et al. | |
| 10,299,951 B2 | 5/2019 | Arbefeuille et al. | |
| 10,390,930 B2 | 8/2019 | Arbefeuille et al. | |
| 10,478,320 B2 | 11/2019 | Shahriari | |
| 10,617,542 B2 | 4/2020 | Chakfe et al. | |
| 10,702,406 B2 | 7/2020 | Swift et al. | |
| 10,744,012 B2 | 8/2020 | Bonsignore et al. | |
| 10,898,357 B2 | 1/2021 | Arbefeuille et al. | |
| 10,987,235 B2 | 4/2021 | Eubanks et al. | |
| 10,987,873 B2 | 4/2021 | Moldave et al. | |
| 11,000,359 B2 | 5/2021 | Torrance et al. | |
| 11,219,540 B2 | 1/2022 | Arbefeuille | |
| 2002/0062133 A1 | 5/2002 | Gilson et al. | |
| 2002/0151956 A1 | 10/2002 | Chobotov et al. | |
| 2002/0177890 A1 | 11/2002 | Lenker | |
| 2002/0188344 A1 | 12/2002 | Bolea et al. | |
| 2002/0193872 A1 | 12/2002 | Trout et al. | |
| 2004/0059406 A1 | 3/2004 | Cully et al. | |
| 2004/0073289 A1 | 4/2004 | Hartley | |
| 2005/0049674 A1 * | 3/2005 | Berra | A61F 2/89 623/1.13 |
| 2005/0131517 A1 | 6/2005 | Hartley et al. | |
| 2005/0131518 A1 | 6/2005 | Hartley et al. | |
| 2005/0131519 A1 | 6/2005 | Hartley | |
| 2005/0131523 A1 | 6/2005 | Bashiri et al. | |
| 2005/0154444 A1 | 7/2005 | Quadri | |
| 2006/0015171 A1 | 1/2006 | Armstrong | |
| 2006/0020319 A1 | 1/2006 | Kim et al. | |
| 2006/0155359 A1 | 7/2006 | Watson | |
| 2006/0184226 A1 | 8/2006 | Austin | |
| 2007/0043425 A1 * | 2/2007 | Hartley | A61F 2/07 623/1.12 |
| 2007/0055360 A1 | 3/2007 | Hanson et al. | |
| 2007/0135904 A1 | 6/2007 | Eidenschink et al. | |
| 2007/0213805 A1 | 9/2007 | Schaeffer et al. | |
| 2007/0233223 A1 * | 10/2007 | Styrc | A61F 2/95 623/1.11 |
| 2007/0244547 A1 | 10/2007 | Greenan | |
| 2008/0091260 A1 | 4/2008 | Pomeranz et al. | |
| 2008/0132988 A1 | 6/2008 | Jordan | |
| 2008/0269867 A1 | 10/2008 | Johnson | |
| 2009/0043377 A1 | 2/2009 | Greenberg et al. | |
| 2009/0248135 A1 | 10/2009 | Bruszewski et al. | |
| 2009/0264990 A1 | 10/2009 | Bruszewski et al. | |
| 2010/0004730 A1 | 1/2010 | Benjamin et al. | |
| 2010/0114290 A1 | 5/2010 | Rasmussen et al. | |
| 2010/0121429 A1 | 5/2010 | Greenan et al. | |
| 2010/0234932 A1 | 9/2010 | Arbefeuille et al. | |
| 2010/0268319 A1 | 10/2010 | Bruszewski et al. | |
| 2010/0316830 A1 | 12/2010 | Hartley et al. | |
| 2011/0077730 A1 | 3/2011 | Fenster | |
| 2011/0190862 A1 | 8/2011 | Bashiri et al. | |
| 2011/0257720 A1 | 10/2011 | Peterson et al. | |
| 2011/0270378 A1 | 11/2011 | Bruszewski et al. | |
| 2012/0035714 A1 | 2/2012 | Ducke et al. | |
| 2012/0221096 A1 | 8/2012 | Roeder et al. | |
| 2012/0271401 A1 | 10/2012 | Bruszewski et al. | |
| 2012/0296360 A1 | 11/2012 | Norris et al. | |
| 2013/0116773 A1 | 5/2013 | Roeder et al. | |
| 2013/0116775 A1 | 5/2013 | Roeder et al. | |
| 2013/0123900 A1 | 5/2013 | Eblacas et al. | |
| 2013/0158648 A1 | 6/2013 | Hartley et al. | |
| 2013/0184806 A1 | 7/2013 | Arbefeuille et al. | |
| 2013/0282102 A1 | 10/2013 | Peterson | |
| 2013/0289713 A1 | 10/2013 | Pearson et al. | |
| 2014/0039597 A9 | 2/2014 | Arbefeuille et al. | |
| 2014/0046428 A1 | 2/2014 | Cragg et al. | |
| 2014/0180378 A1 | 6/2014 | Roeder | |
| 2014/0324150 A1 | 10/2014 | Stephens et al. | |
| 2015/0105819 A1 | 4/2015 | Becking et al. | |
| 2015/0105849 A1 | 4/2015 | Cohen et al. | |
| 2015/0202065 A1 | 7/2015 | Shalev et al. | |
| 2015/0202067 A1 | 7/2015 | Barrand et al. | |
| 2015/0272755 A1 | 10/2015 | Arbefeuille et al. | |
| 2015/0335452 A1 | 11/2015 | Rao et al. | |
| 2016/0100969 A1 | 4/2016 | Lesmeister et al. | |
| 2016/0120667 A1 | 5/2016 | Bolduc et al. | |
| 2016/0184078 A1 | 6/2016 | Choubey et al. | |
| 2016/0199207 A1 | 7/2016 | Treacy et al. | |
| 2016/0296353 A1 | 10/2016 | Skender | |
| 2016/0302950 A1 | 10/2016 | Marmur et al. | |
| 2017/0135807 A1 | 5/2017 | Arbefeuille et al. | |
| 2017/0281382 A1 | 10/2017 | Lostetter et al. | |
| 2018/0071123 A1 | 3/2018 | Arbefeuille et al. | |
| 2018/0153680 A1 | 6/2018 | Greenberg et al. | |
| 2018/0296374 A1 | 10/2018 | Chakfe et al. | |
| 2019/0328556 A1 | 10/2019 | Eubanks et al. | |
| 2019/0350694 A1 | 11/2019 | Arbefeuille et al. | |
| 2020/0246165 A1 | 8/2020 | Arbefeuille et al. | |
| 2020/0352700 A1 | 11/2020 | Torrance et al. | |
| 2021/0100669 A1 | 4/2021 | Arbefeuille et al. | |
| 2021/0236262 A1 | 8/2021 | Torrance et al. | |

FOREIGN PATENT DOCUMENTS

| | | |
|---|---|---|
| CN | 105943213 A | 9/2016 |
| EP | 0786972 B1 | 1/2004 |
| EP | 1847234 A1 | 10/2007 |
| EP | 1847236 A2 | 10/2007 |
| EP | 2471498 A1 | 7/2012 |
| EP | 2501334 A1 | 9/2012 |
| EP | 2517672 A1 | 10/2012 |
| EP | 2735283 A1 | 5/2014 |
| EP | 2740440 A2 | 6/2014 |
| EP | 2745812 A1 | 6/2014 |
| EP | 2745813 A1 | 6/2014 |
| EP | 2749250 A1 | 7/2014 |
| EP | 2749251 A1 | 7/2014 |
| EP | 2606851 B1 | 11/2015 |

(56) References Cited

FOREIGN PATENT DOCUMENTS

| | | |
|---|---|---|
| EP | 3040054 A1 | 7/2016 |
| EP | 3068339 A1 | 9/2016 |
| EP | 3146993 A1 | 3/2017 |
| EP | 3272319 A1 | 1/2018 |
| FR | 2932979 A1 | 1/2010 |
| GB | 2464978 A | 5/2010 |
| WO | WO-97/03624 A1 | 2/1997 |
| WO | WO-97/25002 A1 | 7/1997 |
| WO | WO-99/29262 A1 | 6/1999 |
| WO | WO-99/34749 A1 | 7/1999 |
| WO | WO-01/60285 A1 | 8/2001 |
| WO | WO-02/083038 A2 | 10/2002 |
| WO | WO-03/099108 A2 | 12/2003 |
| WO | WO-2005/034809 A1 | 4/2005 |
| WO | WO-2006/037086 A1 | 4/2006 |
| WO | WO-2009/009376 A2 | 1/2009 |
| WO | WO-2009/148594 A1 | 12/2009 |
| WO | WO-2010/024880 A1 | 3/2010 |
| WO | WO-2010/030370 A1 | 3/2010 |
| WO | WO-2010/127040 A1 | 11/2010 |
| WO | WO-2012/096687 | 7/2012 |
| WO | WO-2012/116368 A2 | 8/2012 |
| WO | WO-2012/145823 A1 | 11/2012 |
| WO | WO-2014/149022 A1 | 9/2014 |
| WO | WO-2014/162306 A2 | 10/2014 |
| WO | WO-2015/059019 A1 | 4/2015 |
| WO | WO-2015/070792 A1 | 5/2015 |
| WO | WO-2016/122862 A1 | 8/2016 |
| WO | WO-2017/218474 A1 | 12/2017 |
| WO | WO-2018/026768 A1 | 2/2018 |

OTHER PUBLICATIONS

International Search Report and Written Opinion for International Application No. PCT/US2018/019510 dated Jul. 11, 2018.

Luo et al, "Stent-grafts for the treatment of TIPS dysfunction: Fluency stent vs. Wallgrent stent," World J Gastroenterol, 19(30): 5000-5005 (2013).

* cited by examiner

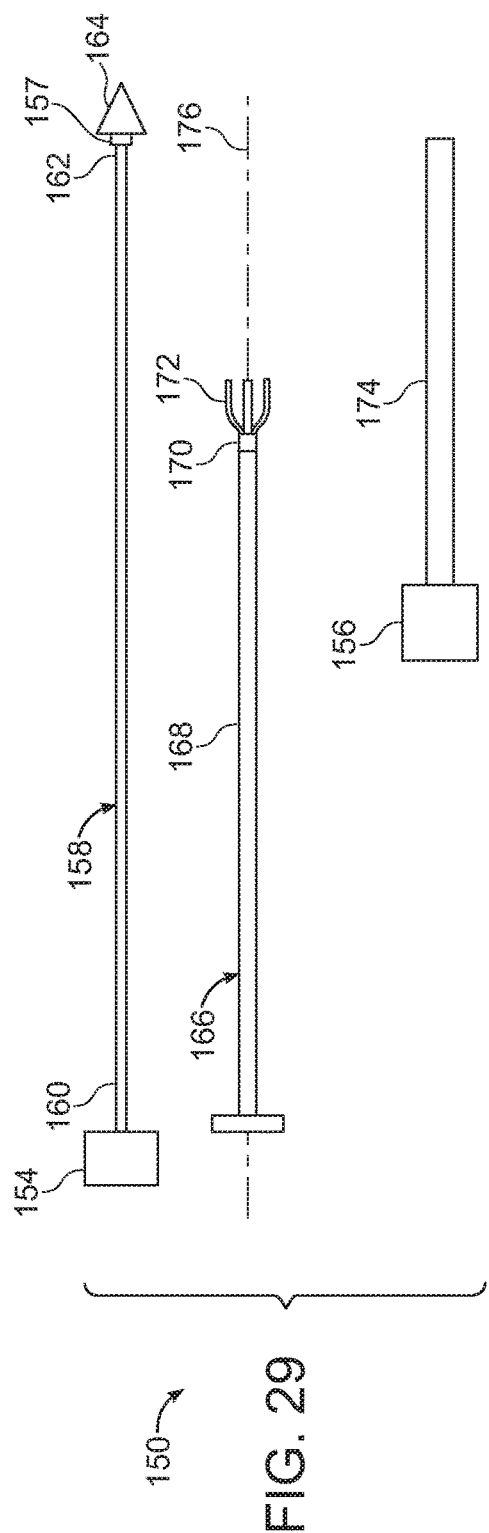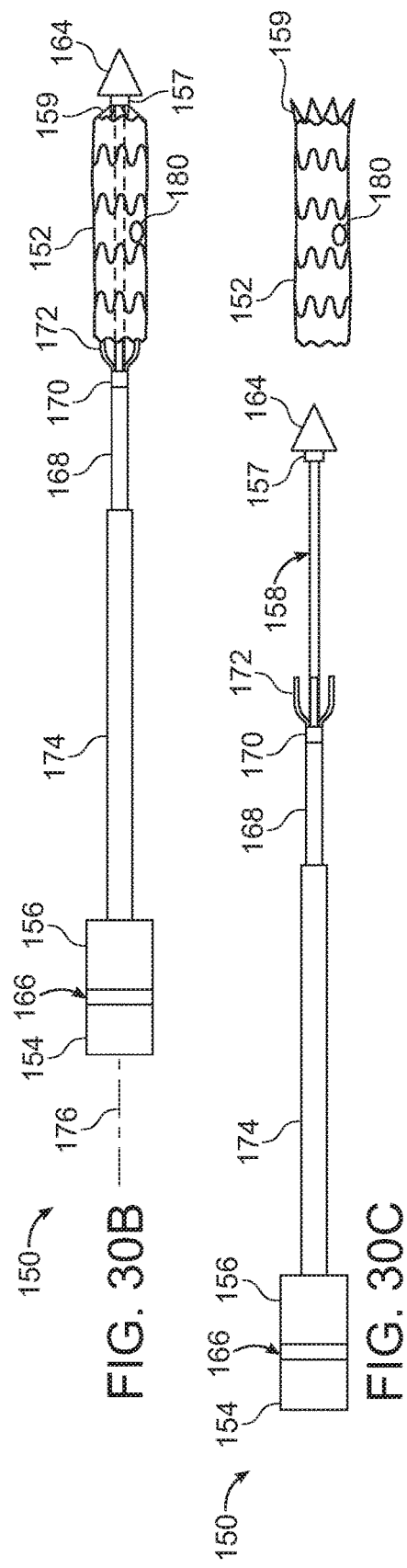

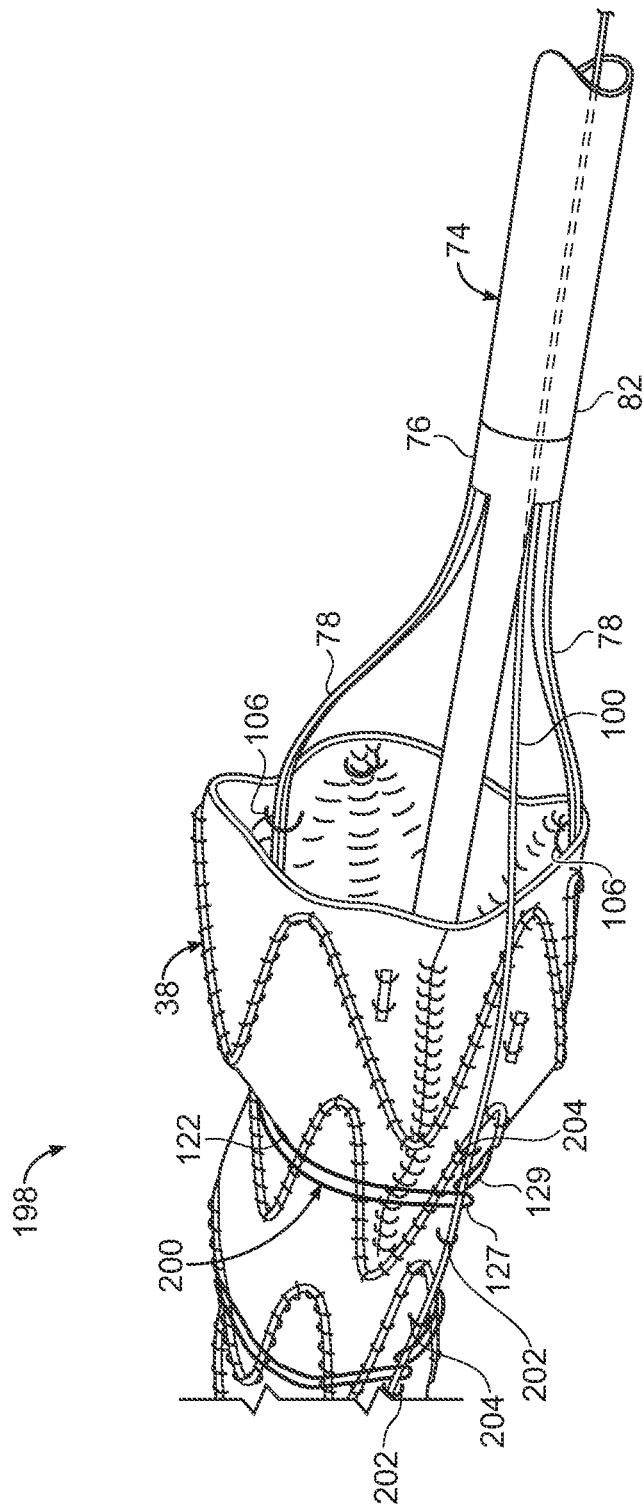
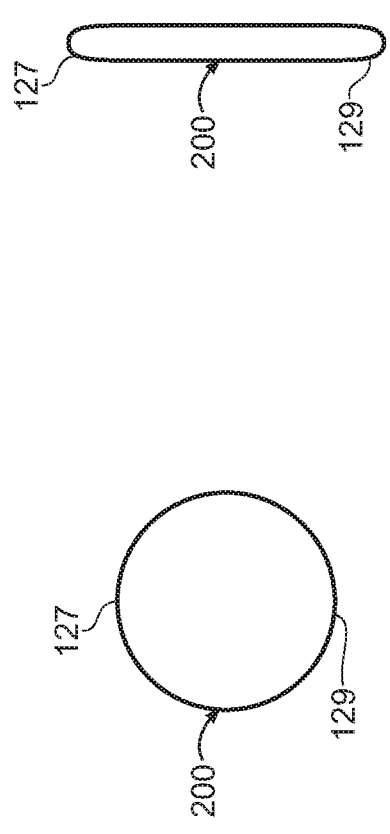
FIG. 31A
FIG. 31B
FIG. 31C

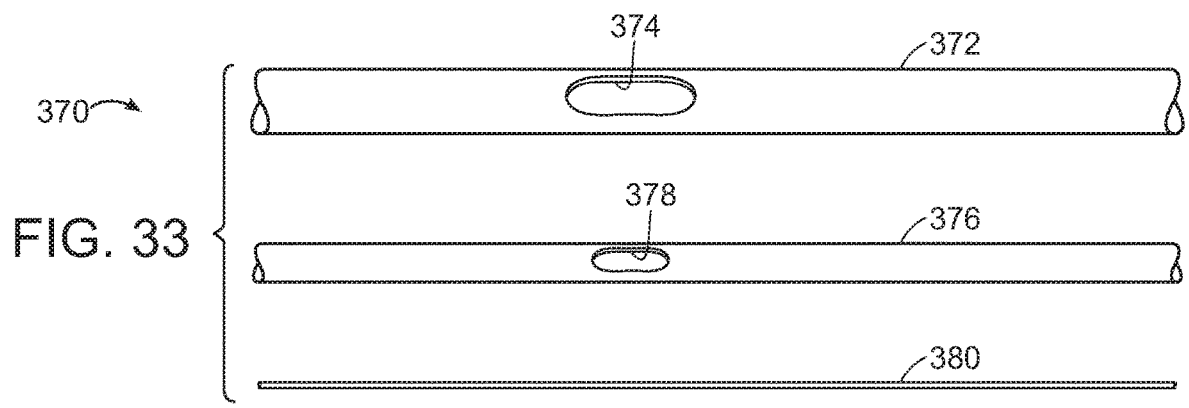
FIG. 33
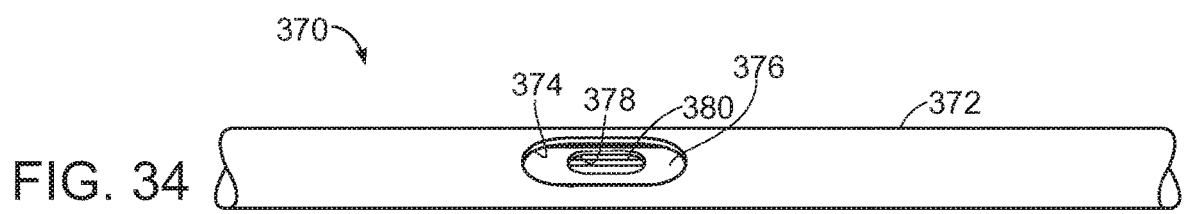
FIG. 34
FIG. 35A
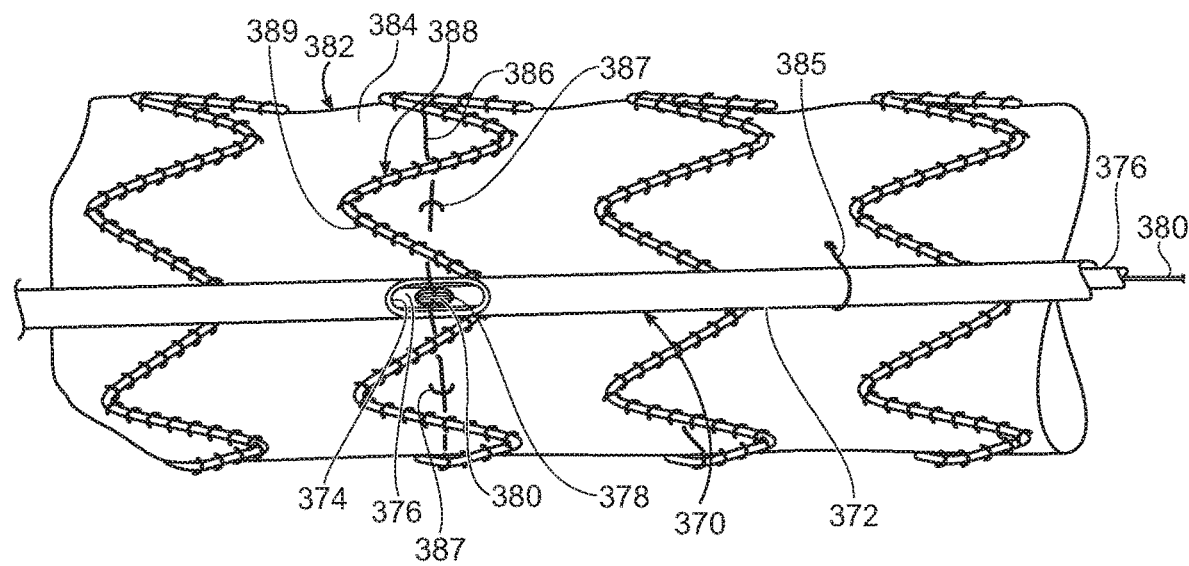

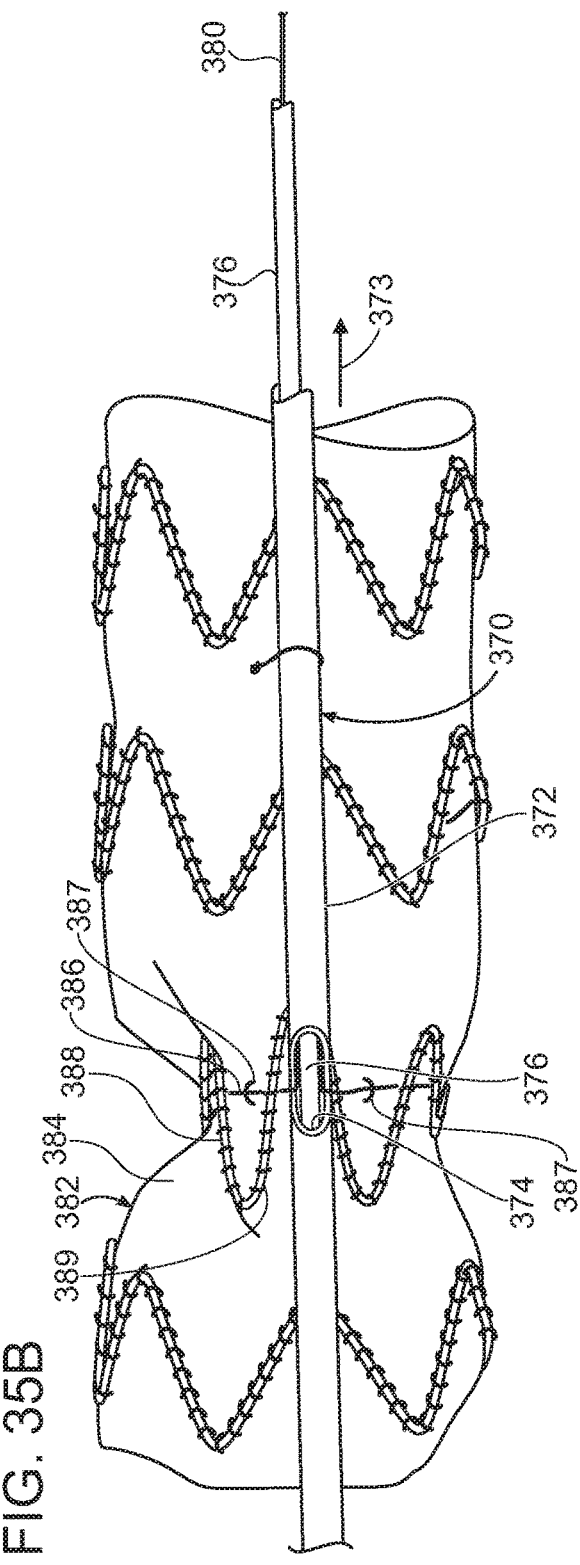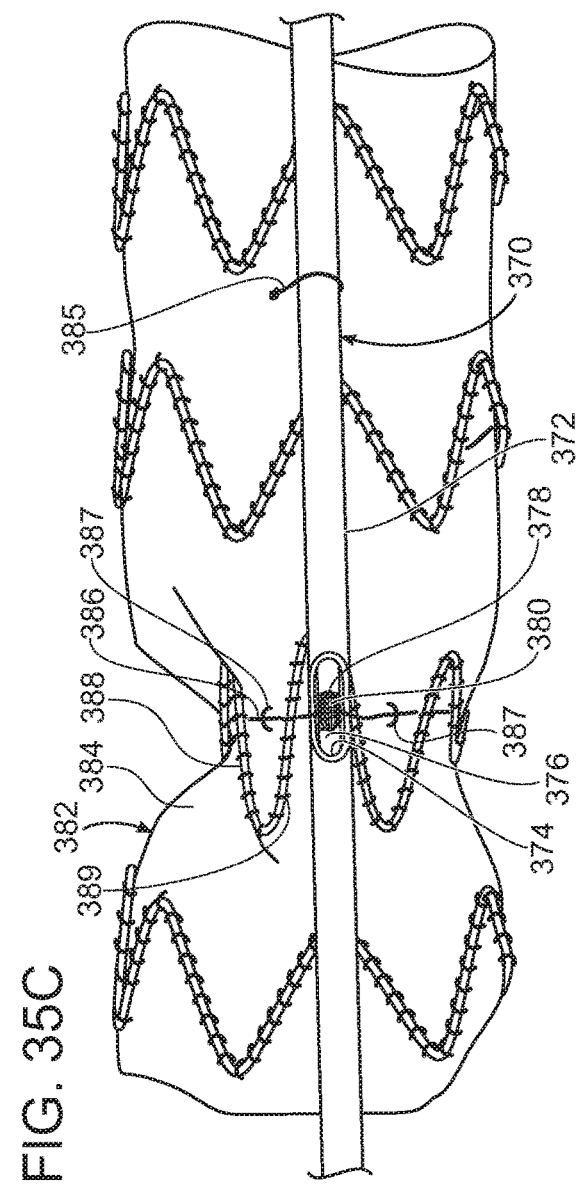
FIG. 35B
FIG. 35C

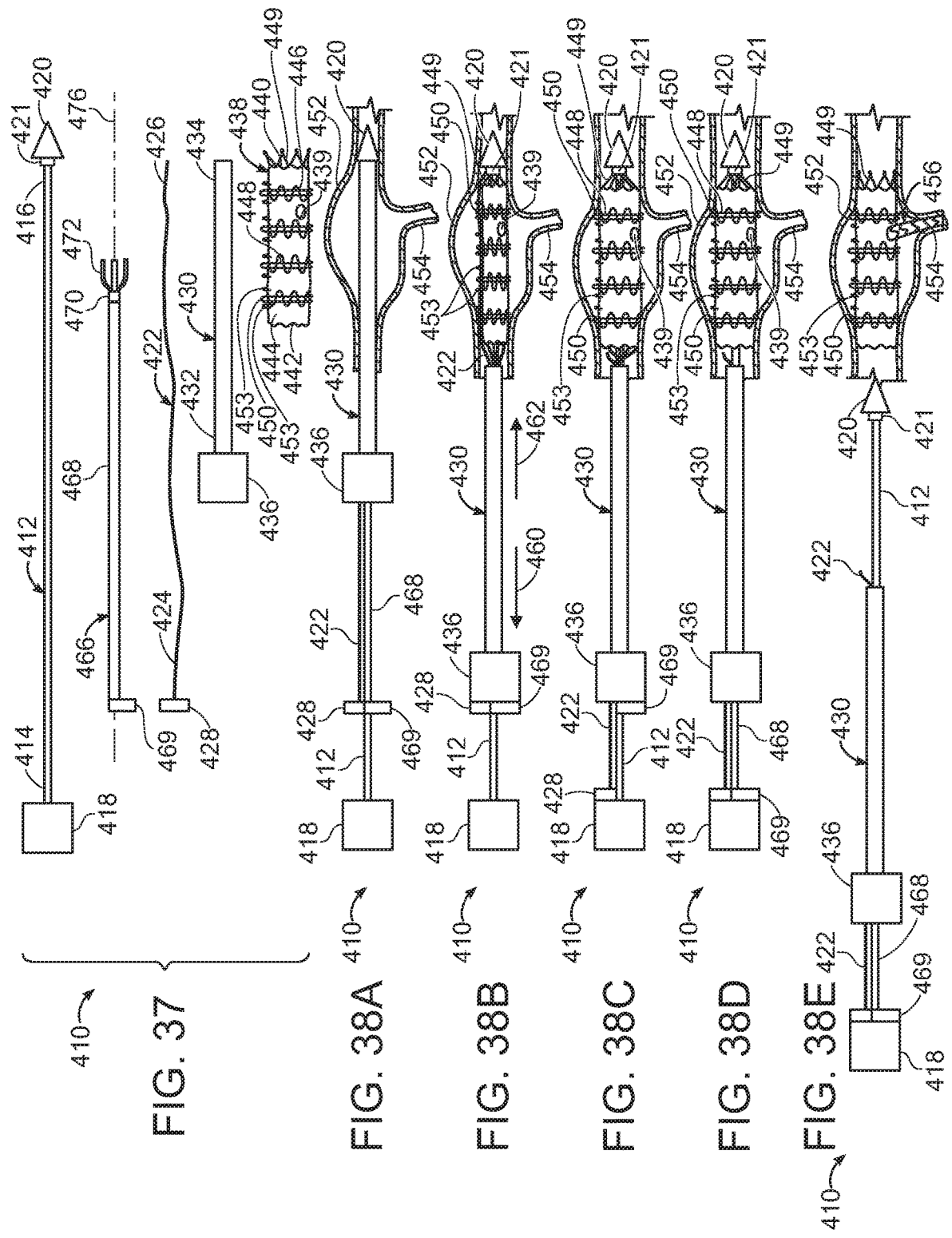

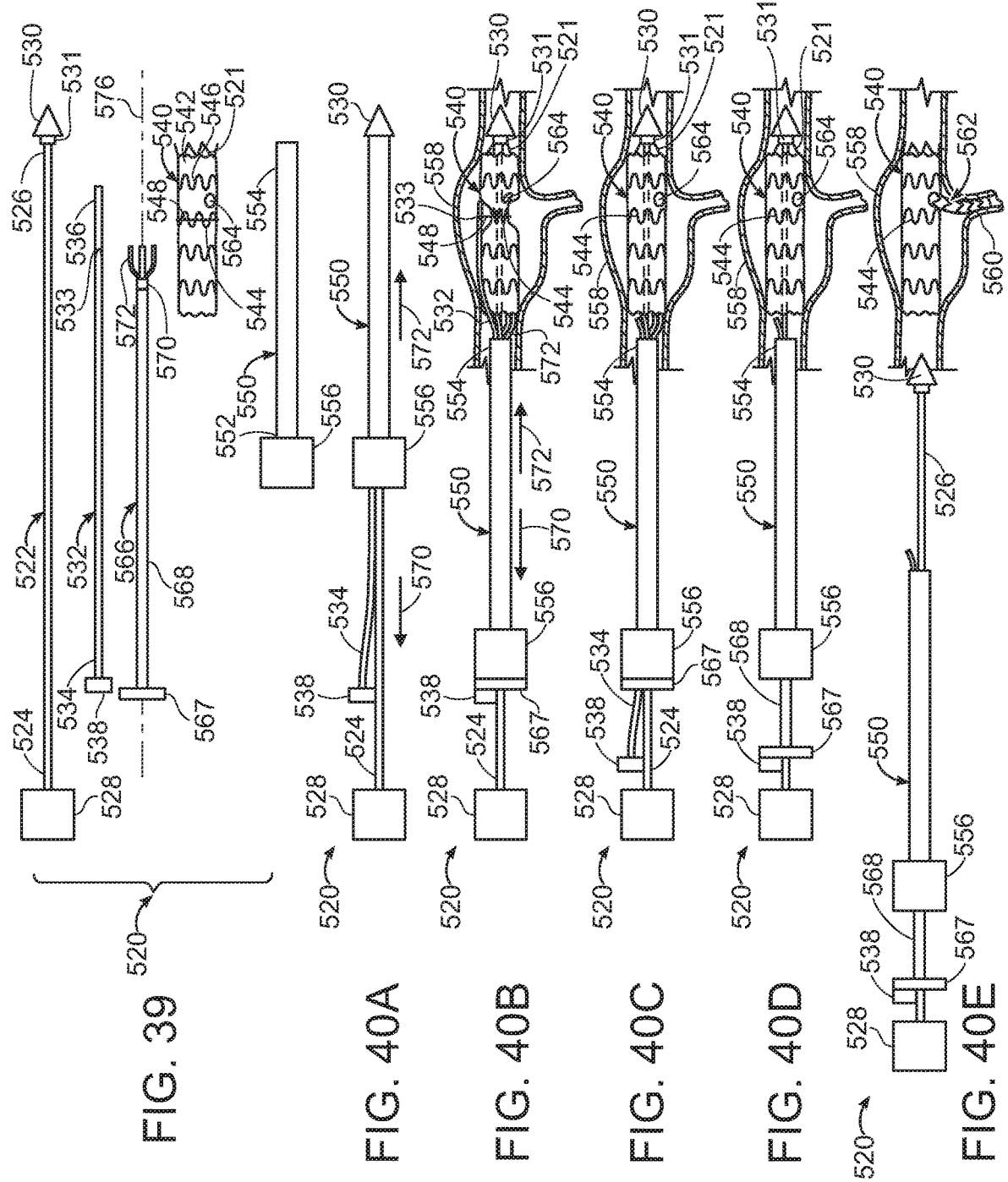

DISTAL TORQUE COMPONENT, DELIVERY SYSTEM AND METHOD OF USING SAME

RELATED APPLICATION

This application is a continuation of International Application No. PCT/US2018/019510, which designated the United States and was filed on Feb. 23, 2018, published in English, which claims the benefit of U.S. Provisional Application No. 62/579,482, filed on Oct. 31, 2017. The entire teachings of the above applications are incorporated herein by reference.

BACKGROUND

Aortic pathologies, including aortic aneurysms, can be treated by open surgical reconstruction, or alternatively, endovascular repair, which is a minimally invasive alternative to open surgical repair. Optimizing a successful outcome of endovascular repair, however, requires assessment of the patient's anatomy and, in the case of an aortic aneurysm, an appropriate stent graft that spans the proximal and distal ends of the aneurysm to insure complete exclusion of the aneurysm sac, anchoring of the stent graft in the aorta, and minimal endoleaks. Also, endoleaks and post-surgical enlargement of the aneurysm site can require additional repair to seal any expansion of the aneurysm sac, and, generally, must be done without significantly compromising blood flow through the surgical site to surrounding viscera and associated structures.

Therefore, a need exists for new and improved endovascular repair devices and methods to treat aortic pathologies, in particular aortic aneurysms.

SUMMARY

The present invention relates to a delivery system that includes a torque component and method of use of the delivery system in treating and repairing aortic vascular damage, such as vascular damage associated with aortic aneurysms in regions of the aorta having arterial branches that supply blood to vital organs and tissue, including thoracic aortic aneurysms, abdominal aortic aneurysms, thoracoabdominal aortic aneurysms, juxtarenal aortic aneurysms and short-neck abdominal aortic aneurysms that employ fenestrated endovascular aortic repair (FEVAR).

In one embodiment, a delivery system of the invention for implanting a stent graft includes a longitudinal body, a guidewire catheter, a radial constraint, and a torque component. The longitudinal body defines a longitudinal axis and includes a proximal handle and a distal handle. The guidewire catheter includes a proximal end and a distal end, and extends from the distal handle of the longitudinal body. The radial constraint is at a stent graft extending about the guidewire catheter. The torque component includes a pushrod, and at least two arms. The pushrod extends about the guidewire catheter and distally from the proximal handle. The arms are disposed radially about and extend distally from the hub, wherein each arm is movable from a constricted state to an expanded state, and whereby the torque component exhibits radial expansion, and whereby application of torque force to the torque component by rotation of the proximal handle about the longitudinal axis causes the stent graft to rotate about the longitudinal axis.

In yet another embodiment of the invention, a delivery system for implanting a stent graft includes a proximal handle and a guidewire catheter extending from the proximal handle, and having a proximal end at the proximal handle and a distal end. A nose cone is fixed at the distal end of the guidewire catheter. A radial constraint that radially constrains a stent graft extending about the guidewire catheter, wherein release of the radial constraint allows radial expansion of the stent graft to thereby at least partially deploy the stent graft. A torque component extends about the guidewire catheter, the torque component including a pushrod extending about the guidewire catheter and distally from the proximal handle, and at least two arms disposed radially about and extending distally from the pushrod, each arm being moveable from a constricted state to an expanded state, whereby the torque component exhibits radial expansion whereby application of torque force to the torque component by rotation of the proximal handle about the longitudinal axis causes the stent graft to rotate about the longitudinal axis.

In another embodiment, the invention is a method of implanting a stent graft at an aneurysm site of a subject. In this embodiment, a stent graft is directed to an aneurysm site of the subject while the stent graft is held in a constricted position by a radial constraint and extends circumferentially about a guidewire catheter that extends distally from a distal handle of a longitudinal body of a delivery device and within the stent graft. The stent graft has a proximal end and a distal end, wherein the distal end of the stent graft is rotationally fixed relative to a torque component, the torque component including a pushrod and at least two arms extending radially about and distally from the pushrod, and the pushrod extending about the guidewire catheter and distally from a proximal handle of the longitudinal body. The proximal handle is rotated to thereby rotate the pushrod and rotationally align the stent graft within the aneurysm site. The radial constraint component is retracted, thereby releasing the stent graft at the aneurysm site. The guidewire catheter is then retracted from the subject, along with the torque component, thereby implanting the stent graft at the aneurysm of the subject.

In still another embodiment, the invention is a method of implanting a stent graft at an aneurysm site that includes the step of advancing a stent graft that is maintained in a constricted state by a radial constraint to an aneurysm site. The stent graft is rotationally aligned by rotation of the stent graft with at least partial assistance of a torque component at a distal end of the stent graft. The radial constraint is removed from the stent graft, and the torque component is retracted from the stent graft, thereby implanting the stent graft at the aneurysm site.

In another embodiment, the invention is a delivery system for implanting a stent graft that includes a proximal handle, a guidewire catheter extending from the proximal handle, and having a proximal end at the proximal handle and a distal end, and a nose cone fixed at the distal end of the guidewire catheter. A stent graft extends about the guidewire catheter and includes a luminal graft component having an outside surface, an inside surface, a proximal open end, a distal open end, and defining a lumen. The stent graft also includes a plurality of stents extending longitudinally along the luminal graft component. A radial constraint at the stent graft includes at least one ligature traversing at least a portion of the struts of the stents of the stent graft, the ligature including ends that, when linked, at least partially radially constrict the stents. A wire extends longitudinally from the luminal graft component and links the ligature ends, thereby radially constricting at least a portion of the stents of the stent graft, whereby retraction of the wire from the ends of the at least one ligature releases the radial constriction by the at least one ligature. A torque component extends about the guidewire catheter and includes a pushrod extending about the guidewire catheter and distally from the proximal handle. At least two arms of the torque component are disposed radially and extend distally from the pushrod, each are being movable from a constricted state to an expanded state, whereby the torque component exhibits radial expansion, and whereby application of torque force to the torque component by rotation of the proximal handle about the longitudinal axis causes the stent graft to rotate about the longitudinal axis.

In still another embodiment, the invention is a delivery system for implanting a stent graft that includes a proximal handle, a guidewire catheter extending from the proximal handle, and having a proximal end at the proximal handle and a distal end. A nose cone is fixed to the distal end of the guidewire catheter. A stent graft extends about the guidewire catheter and includes a luminal graft component having an outside surface, an inside surface, a proximal open end, a distal open end, and defining a lumen. A plurality of stents extend longitudinally along the luminal graft component. A radial constraint at the stent graft includes at least one ligature traversing at least a portion of the struts of stents of stent graft, the ligature including ends that, when linked, at least partially radially constrict the stents. A wire extends longitudinally from the luminal graft component and links the ligature ends, thereby radially constricting at least a portion of the stents of stent graft, whereby retraction of the wire from the ends of the at least one ligature releases the radial constriction by the at least one ligature. A torque component extends about the guidewire catheter and includes a pushrod extending about the guidewire catheter and distally from the proximal handle, and at least two arms disposed radially about and extending distally from the pushrod, each arm being movable from a constricted state to an expanded state, whereby the torque component exhibits radial expansion, and whereby application of torque force to the torque component by rotation of the proximal handle about the longitudinal axis causes the stent graft to rotate about the longitudinal axis.

In another embodiment, the invention is a method that includes the steps of directing a stent graft to an aneurysm of a subject, the stent graft including a luminal graft component and a plurality of radial stents distributed longitudinally along the luminal graft component, at least one of the stents having struts that are joined to define proximal and distal apices, the stent graft being held in a radially constricted position by a radial constraint, the radial constraint including at least one ligature traversing at least a portion of the struts of stents of stent graft, the ligature including ends that, when linked, at least partially radially constrict the stents, the radial constraint also including a wire extending longitudinally along the luminal graft component and linking the ligature ends, thereby radially constricting at least a portion of the stents of stent graft, whereby retraction of the wire from the ends of the at least one ligature releases the radial constriction by the at least one ligature, the radial constraint extending circumferentially about a guidewire catheter that extends distally from a distal handle of a longitudinal body of a delivery device and is within the stent graft, the stent graft having a proximal end and a distal end, and wherein the distal end of the stent graft is rotationally fixed relative to a torque component. The torque component includes a pushrod that extends proximally from and circumferentially about the guidewire catheter and within the stent graft, and at least two arms that extend distally and radially from the pushrod, each arm being moveable from a constricted state to an expanded state whereby the torque component exhibits radial expansion. A proximal handle of longitudinal body is rotated to thereby rotate the pushrod and rotationally align the stent graft within the aneurysm. The radial constraint is retracted, thereby releasing the stent graft at the aneurysm. The guidewire catheter and the torque component are retracted from the subject, thereby implanting the stent graft at the aneurysm of the subject.

In another embodiment, the invention is a delivery system for implanting a stent graft that includes a longitudinal body defining a longitudinal axis and having a proximal handle and a distal handle. A guidewire catheter has a proximal end and a distal end, extends from the distal handle of the longitudinal body. A stent graft extends about the guidewire catheter and includes a luminal graft component having an outside surface, an inside surface, a proximal open end, a distal open end, and defining a lumen. The stent graft also includes a plurality of stents extending longitudinally along the luminal graft component. The radial constraint at the stent graft includes a control rod extends longitudinally along the luminal graft component, and at least one ligature traversing at least one of the stents, and controllably and releasably fixed to the control rod, whereby control of the ligature at the control rod controls radial constriction of the traversed stent. A torque component of the delivery system includes a pushrod extending about the guidewire catheter and distally from the proximal handle, and also includes at least two arms disposed radially about and extending distally from the pushrod, each arm being movable from a constricted state to an expanded state, whereby the torque component exhibits radial expansion, and whereby application of torque force to the torque component by rotation of the proximal handle about the longitudinal axis causes the stent graft to rotate about the longitudinal axis.

This invention has many advantages. For example, the physician can rotate the stent graft after it has been partially deployed, such as by only partially removing the radial constraint. Further, the torque component enables torque to be transmitted to the distal end of a stent graft during delivery, thereby providing greater control over delivery systems that are only able to apply torque to a proximal end of a stent graft. As a consequence, a stent graft can be deployed at a surgical site with more accuracy, less risk of injury to the vasculature of the subject, and without significant risk of distorting the intended shape of the stent graft when implanted at the surgical site.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The same number and different drawings represents the same item. The drawings are not necessarily to scale, emphasis instead being placed upon illustrating embodiments of the present invention.

FIG. 29 is an exploded view of another embodiment of a delivery system of the invention.

FIG. 30A is a side view of the embodiment of the delivery system shown in FIG. 29, in an assembled state, prior to deployment of a stent graft constrained by a radial constraint of delivery system.

FIG. 30B is a side view of the delivery system of FIGS. 29 and 30A, following retraction of the radial constraint from the stent graft.

FIG. 30C is a side view of the delivery system of FIGS. 29, 30A, 30B, following release of a torque component from a distal end of the stent graft, and removal of the delivery system from the stent graft, thereby implanting the stent graft.

FIG. 31A is a perspective view of another embodiment of the invention, wherein the wire of the stent graft delivery system shown in FIG. 18 is longitudinally anchored by anchor loops proximally and distally to ends of a circular ligature linked by the wire to thereby radially constrict the stent graft, and wherein the ligature is a circle that constricts the stent graft by being linked at diametrically opposed points of the circle with the wire.

FIG. 31B is a detail of the circular ligature shown in FIG. 31A.

FIG. 31C is a detail of the circular ligature of FIGS. 31A and 31B when diametrically opposed ends of the circular ligature are arranged to be linked by a wire to thereby secure the circular ligature about the stent graft.

FIG. 33 is an exploded view of components of a detail of another embodiment of a control rod suitable for use in the invention.

FIG. 34 is a side view of the component parts of the control rod represented in FIG. 33 when assembled, showing the wire running through the inner tube and traversing the inner tube fenestration, and the inner tube being within the outer tube, and wherein the fenestrations of the inner tube and the outer tube are aligned.

FIG. 35A is a side view of a detail of the control rod shown in FIGS. 34 and 35, wherein a ligature that traverses the struts of a stent of a radial stent graft of the stent graft delivery system of the invention is threaded between the wire and the inner tube at the inner tube fenestration, and while the inner tube fenestration is aligned with the outer tube fenestration.

FIG. 35B is a side view of the detail of the embodiment shown in FIG. 35A, wherein a stent traversed by a ligature that is linked to the control rod has been radially constricted by proximal retraction of the inner tube relative to the outer tube.

FIG. 35C is a side view of the embodiment shown in FIG. 35A, wherein a stent traversed by a ligature that is linked to the control rod has been radially constricted by rotation of the inner tube about its longitudinal axis, thereby wrapping the ligature about the inner tube.

FIG. 37 is an exploded view of another embodiment of a stent graft delivery system of the invention, including, in addition to a torque component, circular ligature constraints about a stent graft, the diametrically opposed ends of which are linked by a wire, and wherein the stent graft includes a proximal bare stent that can be releasably fixed to an apex capture device at a nose cone of the stent graft delivery system.

FIG. 38A is an assembled side view of the stent graft delivery system shown in FIG. 37, following direction of an introducer sheath of the stent graft delivery system to an aneurysm spanning an arterial branch of the subject.

FIG. 38B is a side view of the embodiment shown in FIG. 38A, following retraction of the introducer sheath from the stent graft, thereby exposing the stent graft in a constricted position.

FIG. 38C is a side view of the embodiment shown in FIGS. 38A and 38B, following retraction of the wire linking diametrically opposed ends of the circular ligatures extending about the stent graft, thereby radially releasing the stent graft.

FIG. 38D is a side view of the embodiment shown in FIGS. 38A-38C, following retraction of the torque component from the distal end of the stent graft.

FIG. 38E is a side view of the embodiment shown in FIGS. 38A-38D, following release of the bare stent from the apex capture device, and retraction of a remainder of the delivery system not implanted at the aneurysm site from the stent graft, and following implantation of a branch prosthesis through a fenestration and into the arterial branch spanned by the aneurysm.

FIG. 39 is an exploded view of another embodiment of a stent graft delivery system of the invention, including, in addition to a torque component, a control rod that is releasably attached to a ligature about a stent graft that can control radial contraction of a stent of the stent graft traversed by the ligature.

FIG. 40A is a side view of the embodiment shown in FIG. 39, following assembly, wherein the stent graft is loaded into an introducer sheath of the stent graft delivery system.

FIG. 40B is a side view of the embodiment shown in FIG. 40A, following retraction of the introducer sheath, thereby exposing the stent graft, while it is radially constricted at a stent of a stent graft spanned by the ligature wrapped about the control rod.

FIG. 40C is a side view of the embodiment shown in FIGS. 40A and 40B, following rotation of the control rod about its axis to allow radial expansion of stent graft traversed by the ligature, and following release of the ligature from the control rod which is retracted in a proximal direction.

FIG. 40D is a side view of the embodiment shown in FIGS. 40A-40C, following proximal retraction of the torque component from the distal end of the stent graft.

FIG. 40E is a side view of the embodiment shown in FIGS. 40A-40D, following release of the bare stent at the proximal end of the stent graft from the apex capture device at the nose cone of the stent graft delivery system, and following release of the stent graft delivery system not implanted at the aneurysm site and implantation of a branch prosthesis through a fenestration of the stent graft into an arterial branch spanned by the aneurysm.

DETAILED DESCRIPTION

The invention is generally directed to delivery systems for implanting prostheses and to methods for use in treating vascular disease, such as may be beneficial or required during fenestrated endovascular aortic aneurysm repair, where the physician needs to rotate a stent graft after it is partially deployed by, for example, partial expansion within an arterial lumen.

The features and other details of the invention, either as steps of the invention or as combinations of parts of the invention, will now be more particularly described and pointed out in the claims. It will be understood that the particular embodiments of the invention are shown by way of illustration and not as limitations of the invention. The principle features of this invention can be employed in various embodiments without departing from the scope of the invention.

When reference is made herein to a prosthesis, also referred to herein as a "stent graft," "stent graft prosthesis," or "vascular prosthesis," to be delivered, or implanted in a patient, the word "proximal" means that portion of the prosthesis or component of the prosthesis that is relatively close to the heart of the patient and "distal" means that portion of the prosthesis or component of the prosthesis that is relatively far from the heart of the patient.

When, however, reference is made to a delivery system or a component of a delivery system employed to deliver, or implant, a prosthesis, the word, "proximal," as employed herein, means closer to the clinician using the delivery system. When reference is made to a delivery system or a component of a delivery system, "distal," as that term is employed herein, means, further away from the clinician using the delivery system.

For clarity, the word "proximate" means "close to," as opposed to the meanings ascribed to "proximal" or "distal" described above with respect to either the prosthesis or a delivery system.

A description of example embodiments of the invention follows.

Figure 1:
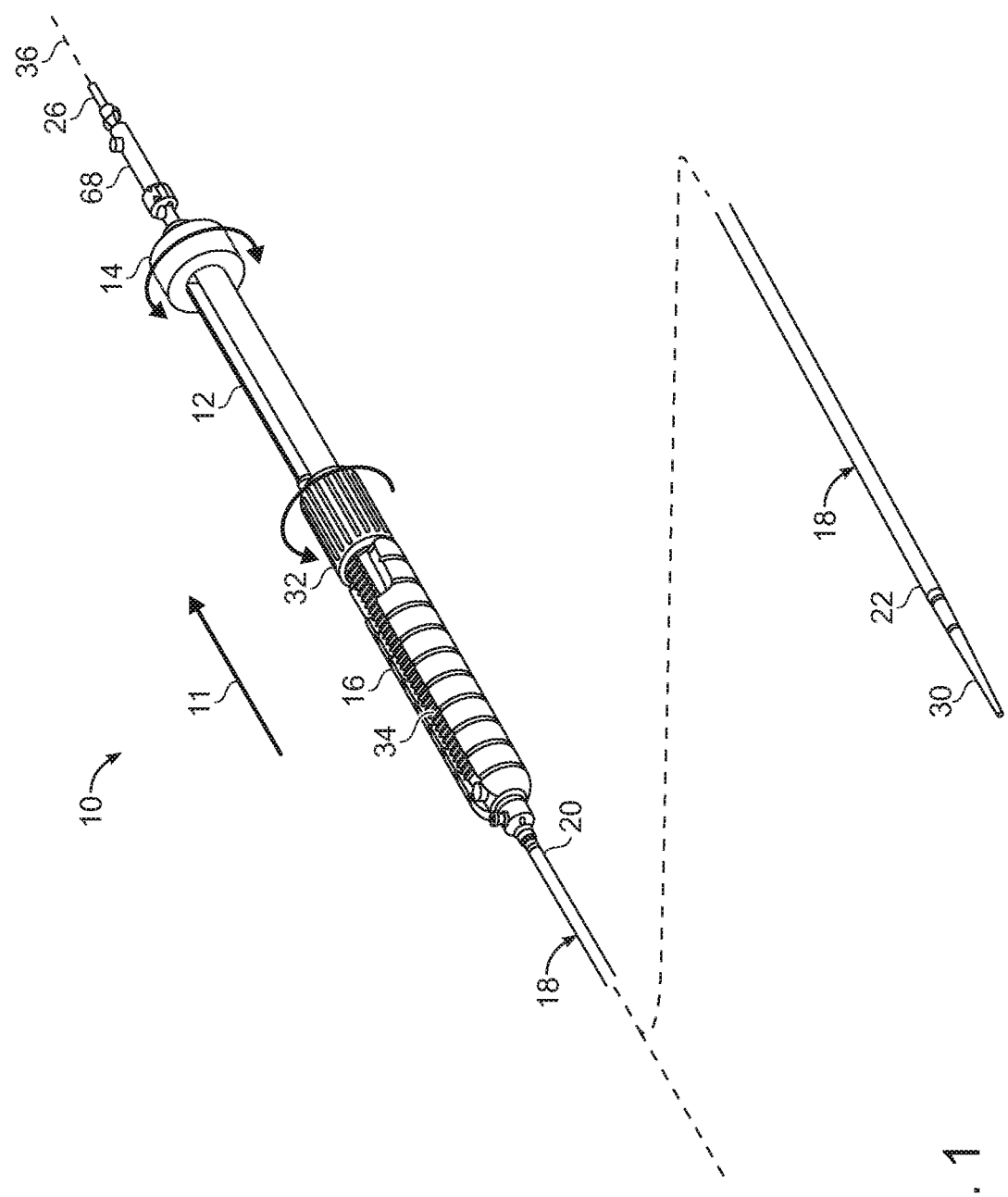
FIG. 1 is a perspective view of one embodiment of a delivery system of the invention for implanting an arterial stent graft.

One embodiment of a delivery system of the invention for implanting a stent graft prosthesis is shown in FIG. 1. As shown therein, delivery system 10 includes longitudinal body 12 having proximal handle 14 at a proximal end and distal handle 16 at a distal end. Introducer sheath 18 (an introducer sheath is an embodiment of a radial constraint) extends distally from distal handle 14, and includes proximal end 20 and distal end 22. Guidewire catheter 24 (FIG. 3) includes proximal end 26 and distal end 28 (FIG. 2), and extends from distal end 16 of longitudinal body 12. Guidewire catheter 24 extends within introducer sheath 18 and through longitudinal body 12. Proximal end 26 of guidewire catheter 24 extends from proximal handle 14 of longitudinal body 12.

Figure 2:
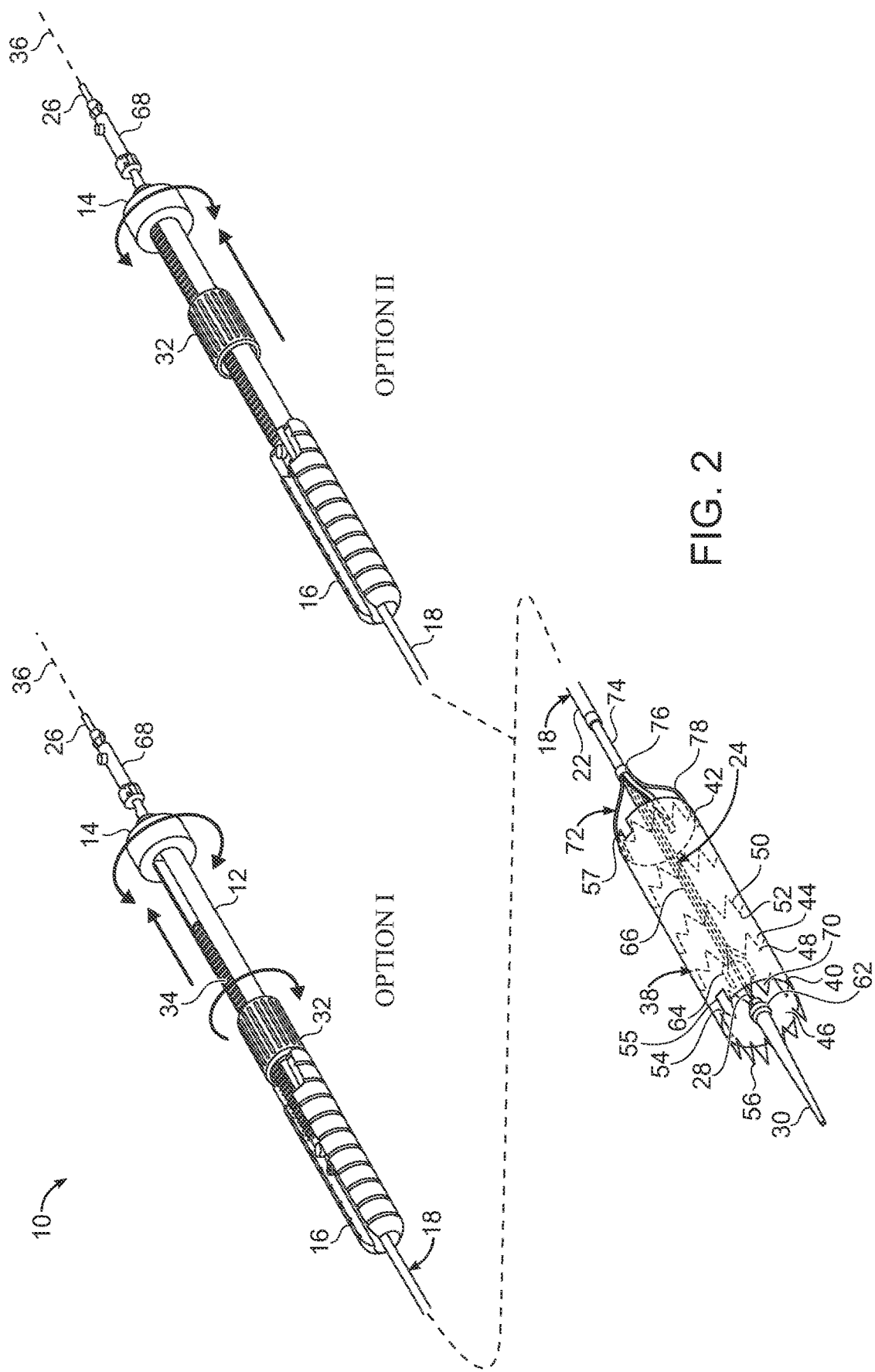
FIG. 2 is a perspective view of the delivery system of FIG. 1 of the invention showing two options for retracting an introducer sheath from about the stent graft prosthesis.

Nose cone 30 is fixed to distal end 28 (FIG. 2) of guidewire catheter 24. Guidewire catheter 24 and nose cone 30 define a luminal channel through which a guidewire (not shown) can extend. Introducer sheath 18 is movable along longitudinal axis 36 of delivery device 10 in a proximal direction 11 relative to a surgeon operating delivery device 10, by retracting introducer sheath 18 relative to distal handle 16 of longitudinal body 12. In one embodiment, for example, as shown in FIG. 2, introducer sheath 18 can be retracted by rotation of lead screw nut 32 that is threaded in mating configuration with track 34 to which introducer sheath 18 is fixed, directly or indirectly. Option I of FIG. 2 shows rotation of a lead screw nut 32 causing longitudinal movement of track 34 and, therefore, introducer sheath 18 along longitudinal axis 36 of delivery device 10. Alternatively, lead screw nut 32 can be drawn back directly along longitudinal body 12 without rotation to thereby retract introducer sheath 18, as shown in Option II. As can be seen, in either option, retraction of introducer sheath 18 at least partially exposes stent graft 38, while guidewire catheter 24 and nose cone 30 remain fixed relative to longitudinal body 12.

In an alternative embodiment, not shown, introducer sheath 18 is not linked to track 34, but rather to distal handle 16 of longitudinal body 12, and longitudinal body 12 includes a proximal handle component that directs guidewire catheter 24 and, consequently, stent graft 38 distally from within distal end 22 of introducer sheath 18 to thereby release stent graft 38. As with the embodiment represented in FIGS. 1 and 2, once stent graft 38 is released, guidewire catheter 24 and nose cone 30, as well as introducer sheath 18 are all retracted and withdrawn from the subject.

As shown in FIG. 2, stent graft 38 includes proximal end 40 and distal end 42. Luminal graft component 44 of stent graft 38 defines lumen 46. Stents 48 are self-expanding and are formed of struts 50 that are connected to form proximal apices 52 and distal apices 54. In an embodiment, stent graft 38 includes bare stent 56 at proximal end 40. Bare stent 56 is secured to luminal graft component 44 at proximal end 40 of stent graft 38 by distal apices 54 of bare stent 56, for example, with sutures, biocompatible adhesive, or other suitable techniques known to those skilled in the art. Luminal graft component 44 defines a lumen extending from proximal end 40 to distal end 42. In certain embodiments, luminal graft component 44 can include scalloped portions 55,57, at proximal end 40 and distal end 42, respectively. Luminal graft component 44 is formed of a suitable material, such as are known to those skilled in the art, including, for example, expanded polytetrafluoroethylene (PTFE), such as ePTFE, and polyethylene terephthalate (PET), such as woven polyester. Stents 48 and bare stent 56 are formed of a suitable material, such as shape memory alloys (Nitinol) or stainless steel.

Figure 3:
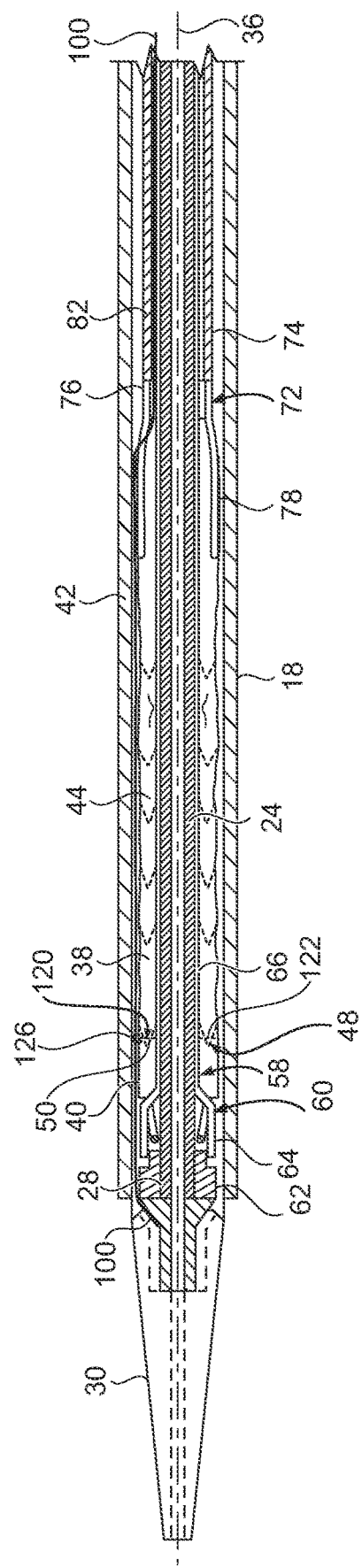
FIG. 3 is a cross-sectional view of the delivery system of the invention shown in FIG. 1, before deployment of the stent graft.

FIG. 3 is a cross-sectional view of a distal portion of delivery device 10 prior to deployment of stent graft 38 from within introducer sheath 18. In one specific embodiment, bare stent 38 is in a first, captured state, in which proximal apices of bare stent 38 are fixed to apex capture assembly 58 of delivery device 10. In one embodiment, apex capture assembly 58 includes proximal capture component 60 and distal capture component 62. Proximal capture component 60 includes tines 64 that extend distally from apex capture catheter 66, which surrounds guidewire catheter 24 and is fixed to guidewire catheter 24 by proximal clasp assembly 68, shown in FIG. 2, at proximal end 26 of guidewire catheter 24. When in a captured state, shown in FIG. 3, tines 64 extend through openings 70 (FIG. 2) defined by bare stent 56 at luminal graft component 44 of stent graft 38, thereby preventing radial expansion of bare stent 56 at proximal end 40 of stent graft 38. Release of apex capture catheter 66 from guidewire catheter 24 at proximal clasp assembly 68 enables proximal movement of apex capture catheter 66 and proximal capture component 60 from distal capture component 62 to thereby release bare stent 56 from tines 64, thereby releasing bare stent 56 from the captured state to a released state.

Torque component 72, includes pushrod 74, hub 76, and at least two arms 78. Pushrod 74 has proximal end (not shown) and distal end 82, and extends about guidewire catheter 24 and distally from proximal handle 14. Although not shown, proximal end of pushrod 74 is fixed to proximal handle 14 of longitudinal body 12. Proximal handle 14 is rotatable about longitudinal body 12 to thereby cause pushrod 74 to rotate about guidewire catheter 24. Optionally, proximal handle 14 can be locked with guidewire catheter 24, and apex capture catheter 66, whereby rotation of proximal handle 14 causes axial rotation of guidewire catheter 24 and apex capture catheter 66. Hub 76 defines lumen 88 and is fixed to distal end 82 of pushrod 74. At least two arms 78 extend distally from hub 76 and are distributed radially about apex capture lumen 66.

Figure 4:
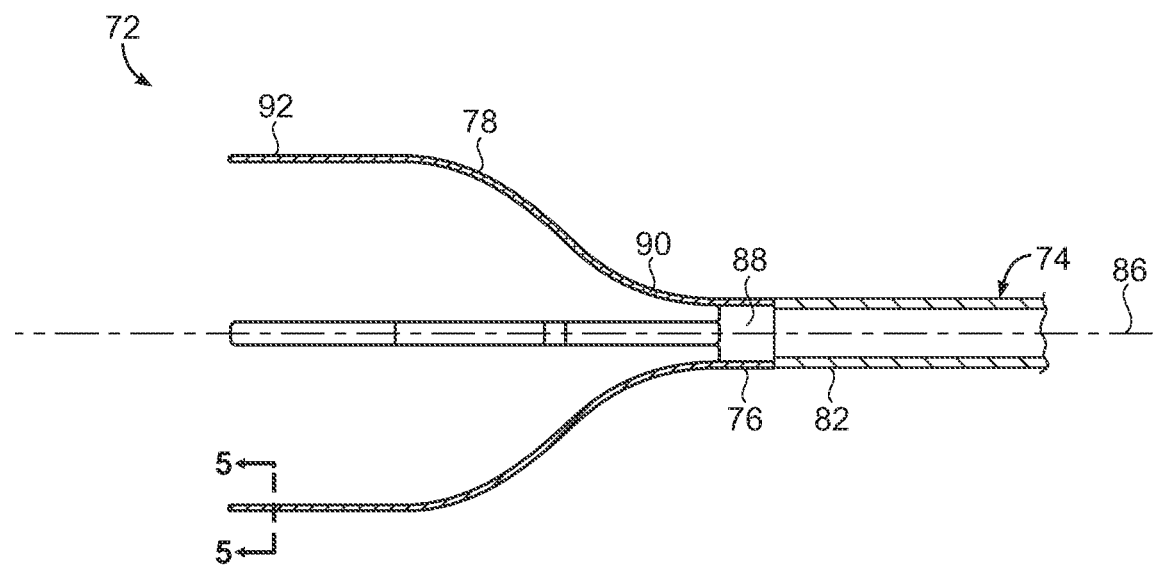
FIG. 4 is a cross-sectional view of one embodiment of a distal end of a torque component of a delivery system of the invention.

Each arm 78 is expandable from a constricted state, shown in FIG. 3, to an expanded state, shown in FIG. 4, by release of arms 78 from the constricted state. In one embodiment, arms 78 are self-expanding from the constricted state to the expanded state. Arms 78 are fixed to hub 76 of torque component 72 which, in turn, is fixed to pushrod 74 of torque component 72.

Figure 5:
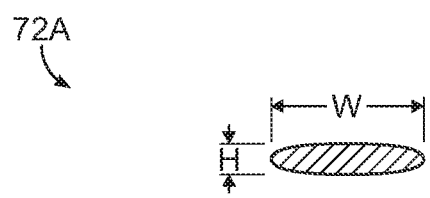
FIG. 5 is a cross-sectional representation of an arm of the torque component shown in FIG. 4.

As can be seen in FIG. 5, width (W) of arm 78 is greater than height (H) of arm 78. When viewed at an angle normal to longitudinal axis of hub, as shown in FIG. 4, arms have a curvilinear shape in the expanded state. In various embodiments, torque component 72 can include two, three, or four arms. Arms 78 each have proximal end 90 and distal end 92. Optionally, proximal ends 90 of arms 78 are evenly spaced about longitudinal axis 86 at the circumference of hub 76. In one embodiment, each of arms 78 independently has a length in a range of between about 1 inch and about 5 inches.

Hub 76 and arms 78 are formed of a suitable material, such as Nitinol, or other suitable shape-memory alloy, stainless steel, titanium or a plastic.

Figure 6:
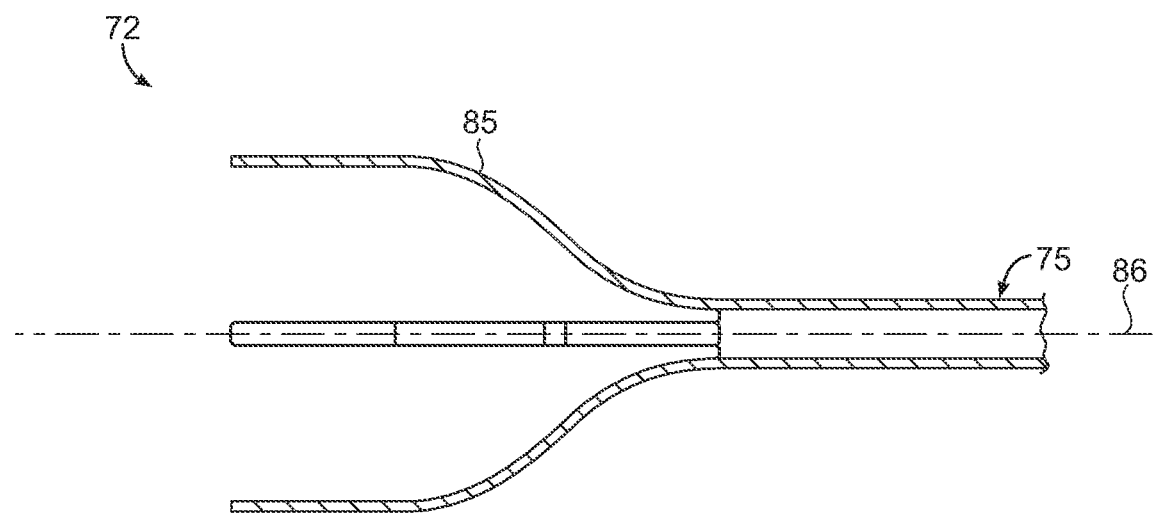
FIG. 6 is a cross-sectional view of another embodiment of a distal end of a torque component of a delivery system of the invention.
Figure 7:
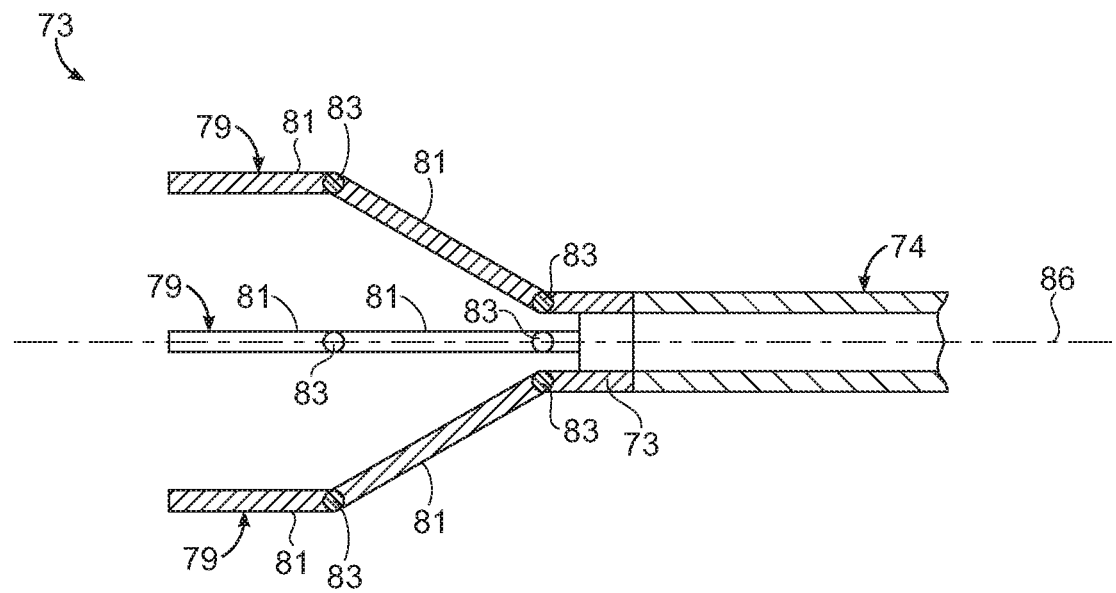
FIG. 7 is a side view of an alternative arm of the torque component of the invention.

FIG. 6 is a cross-sectional view of another embodiment of the torque component of FIG. 4, but wherein the torque component lacks a hub component. As shown therein, torque component 72A includes arms 85 connected to pushrod 75, or extensions of pushrod 75. Alternatively, torque component 73 includes arms that are articulated members 79, as shown in FIG. 7. In this embodiment, members 79 include segments 81 joined to each other and to hub 88 by hinges 83. Members 79 are formed of a suitable material, such as Nitinol or some other shape-memory alloy, stainless steel, titanium, or a plastic.

Figure 8:
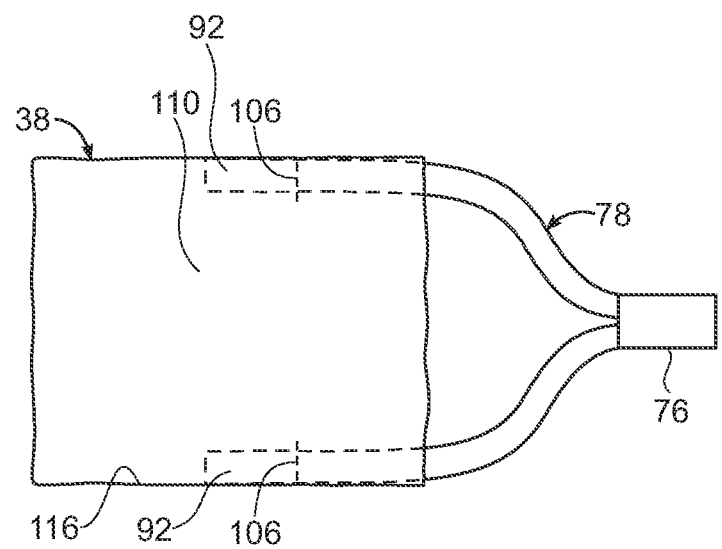
FIG. 8 is a side view of one embodiment of a delivery system of the invention showing relative positioning of a stent graft to be delivered and a portion of a torque component of the delivery system of the invention.
Figure 9:
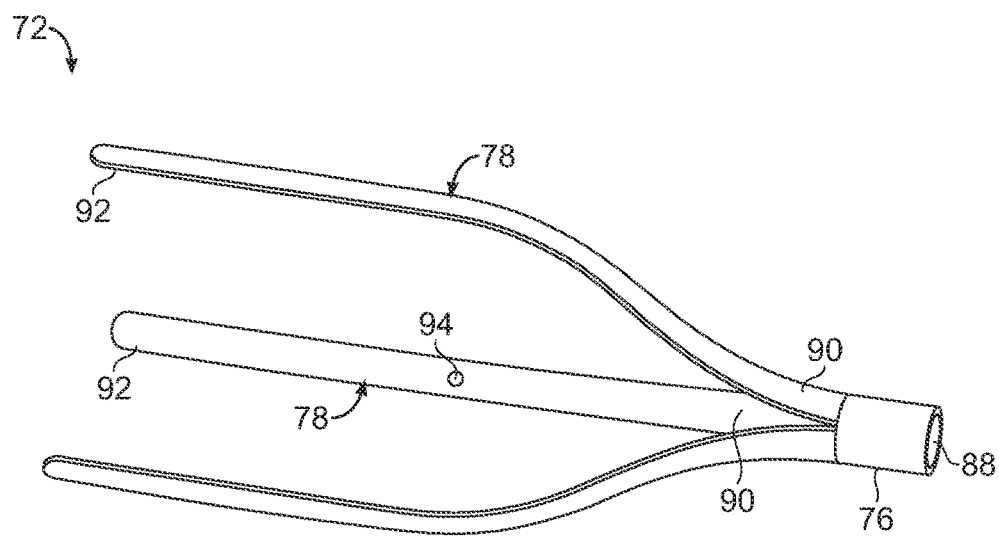
FIG. 9 is a perspective view of another embodiment of a torque component of the invention, wherein an arm of the torque component defines an opening.
Figure 10:
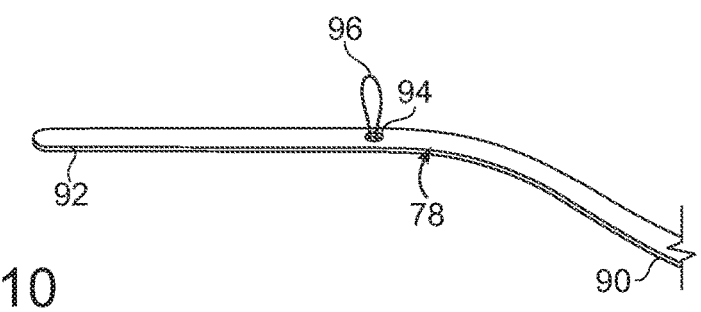
FIG. 10 is a perspective view of another embodiment of the arm of the delivery system of the invention defining an opening, wherein a suture ring extends from the opening.
Figure 11:
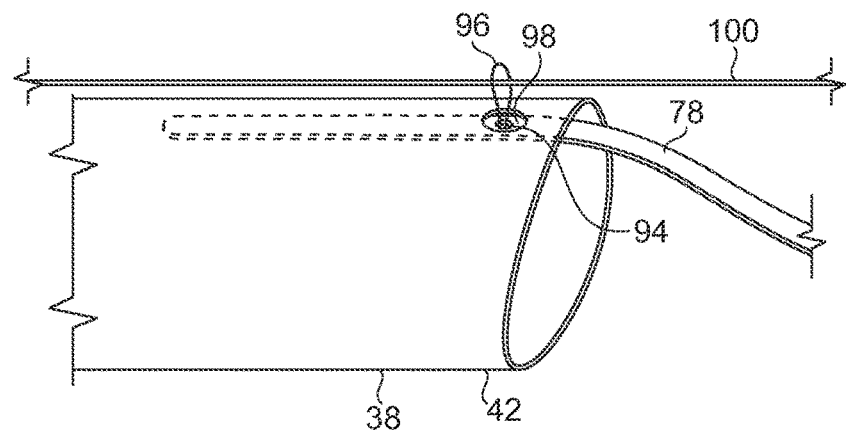
FIG. 11 is a side view of another embodiment of the arm and suture ring shown in FIG. 10, wherein the distal end of a stent graft is secured to the arm by the suture ring, which extends through an opening defined by the distal end of the stent graft, and a release wire that extends through the suture ring of the invention.
Figure 22:
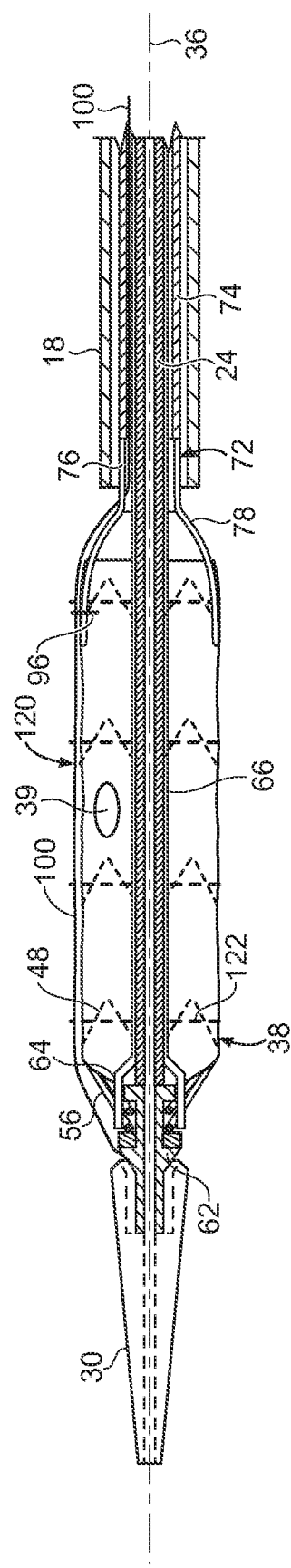
FIG. 22 is a cross-section of an embodiment of the delivery system shown in FIG. 21, wherein the introducer sheath has been fully retracted from the stent graft and also from arms of a torque component of the delivery system of the invention.

Prior to deployment, distal ends 92 of arms 78 engage with stent graft 38, as shown, for example, in FIG. 8, and secured by sutures 106 within lumen 46 of stent graft 38. In another embodiment, shown in FIGS. 9-11, at least one arm 78 defines opening 94 through which suture ring 96 extends and to which suture ring 96 is fixed. Suture ring 96 also extends through opening 98 defined by stent graft 38. Release wire 100 extends longitudinally along delivery device 10 is tucked into, or under, nose cone 30, as shown in FIG. 3, and through suture ring 96, as shown in FIG. 11, thereby securing distal end 42 of stent graft 38 to arm 78. An advantage of wire 100 extending through suture loop 96 is gained when guidewire catheter 24 and apex capture assembly 58, to which stent graft 38 is held in a captured state, has been exposed by retraction of introducer sheath 18, as shown in FIG. 22, are moved longitudinally within artery along longitudinal axis 36 in order to properly position stent graft 38. Suture 96 is held in place at opening 98 of stent graft 38 by wire 100 extending through suture 96, and prevents longitudinal collapse of stent graft that would otherwise occur by friction between stent graft 38 and arterial wall during longitudinal positioning that includes proximal movement (toward the clinician) of guidewire catheter 24 and apex capture assembly 58.

Figure 12:
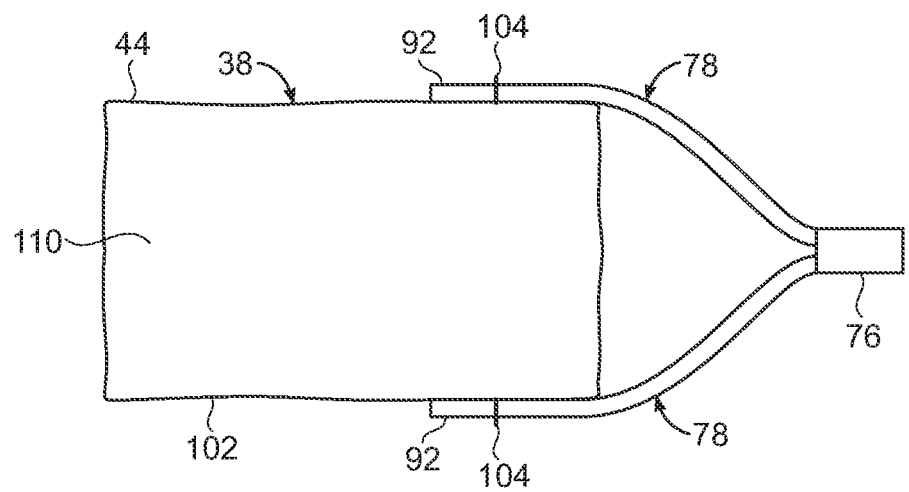
FIG. 12 is a side view of an alternative arrangement of a stent graft and a portion of the torque component of the delivery system of the invention.
Figure 13:
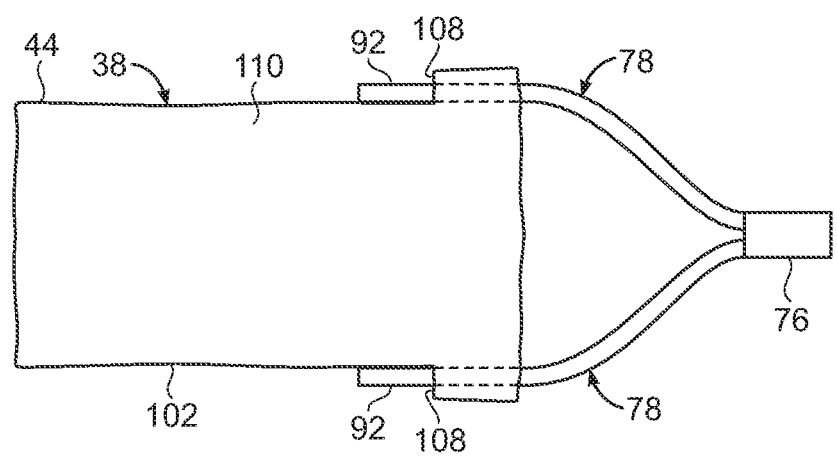
FIG. 13 is a side view of yet another arrangement of the stent graft relative to a portion of the torque component of the delivery system of the invention.
Figure 14:
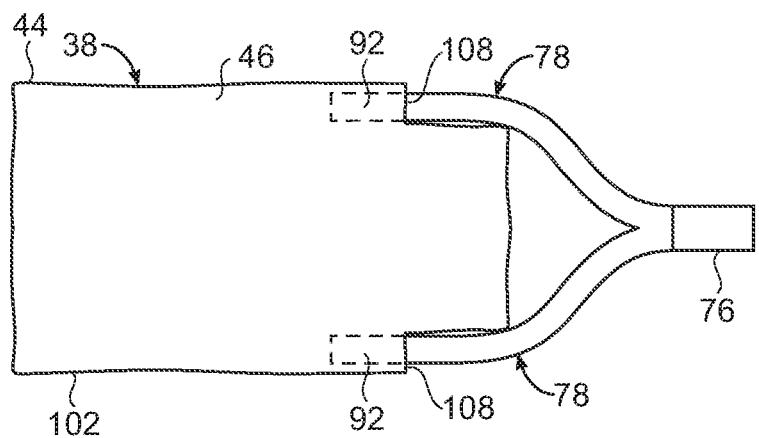
FIG. 14 is a side view of still yet another embodiment of an arrangement connecting the stent graft and a portion of the torque component of the delivery system of the invention.
Figure 15:
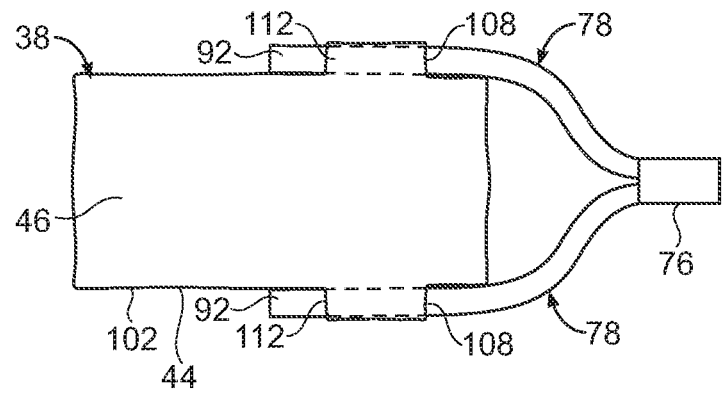
FIG. 15 is a side view of another embodiment of an arrangement connecting the stent graft and a portion of the torque component of the delivery system.

Alternative arrangements for securing distal end 42 of stent graft 38 to arms 78 are shown in FIGS. 12 through 17. Specifically, as shown in FIG. 12, arms 78 can extend along outside surface 102 of stent graft 38 and can be releasably secured thereto by external sutures 104 fixed to luminal graft component 44 of stent graft 38. As shown in FIG. 13, distal end 42 of stent graft 38 defines slots 108 through which arms 78 extend distally from lumen 46 of stent graft to an outside surface 102 of stent graft 38. Alternatively, as shown in FIG. 14, arms 78 extend distally from outside surface 102 of stent graft 38 through slots 108 to lumen 46 of stent graft 38. In yet another embodiment, shown in FIG. 15, arms 78 can each extend through a plurality of slots 108, 112, such as distally from outside surface 102 of stent graft 38 through first slot 108 to lumen 46 of stent graft and back through second slot 112 to the outside portion 102 of stent graft 38.

Figure 16:
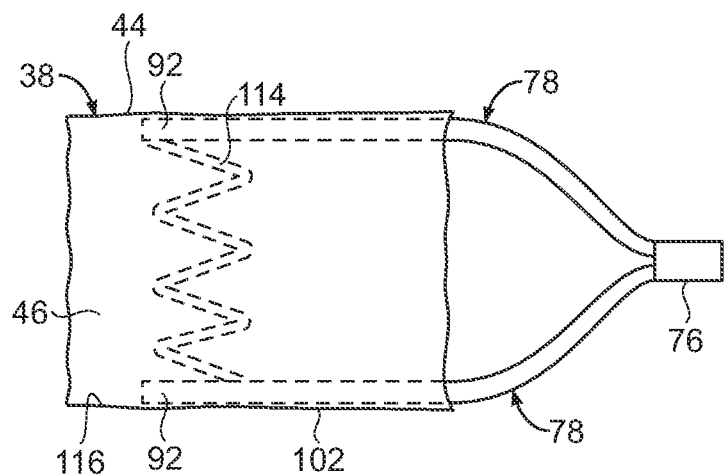
FIG. 16 is a side view of another embodiment of an arrangement of a stent graft, and an internal stent of the stent graft, relative to the torque component of the delivery system.
Figure 17:
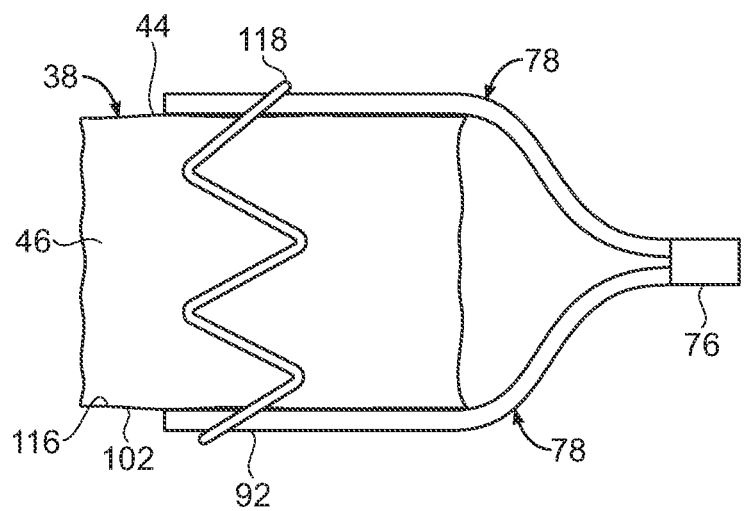
FIG. 17 is a side view of another embodiment of arrangement connecting a stent graft, in particular, an external stent of the stent graft, and the torque component of the delivery device.

As shown in FIGS. 16 and 17, a stent component of stent graft 38 can be employed to secure arms 78 to stent graft 38. As shown in FIG. 16, for example, stent 114 secured to inside wall 116 of luminal graft component 44 can assist in securing arm 78 to stent graft 38 by placement of arm 78 between stent 114 and luminal graft component 44. Alternatively, stent 118 extending about outside surface 102 of luminal graft component 44 of stent graft 38 can assist in securing arms 78 by placement of arms 78 between luminal graft component 44 and stent 118, as shown in FIG. 17.

Figure 18:
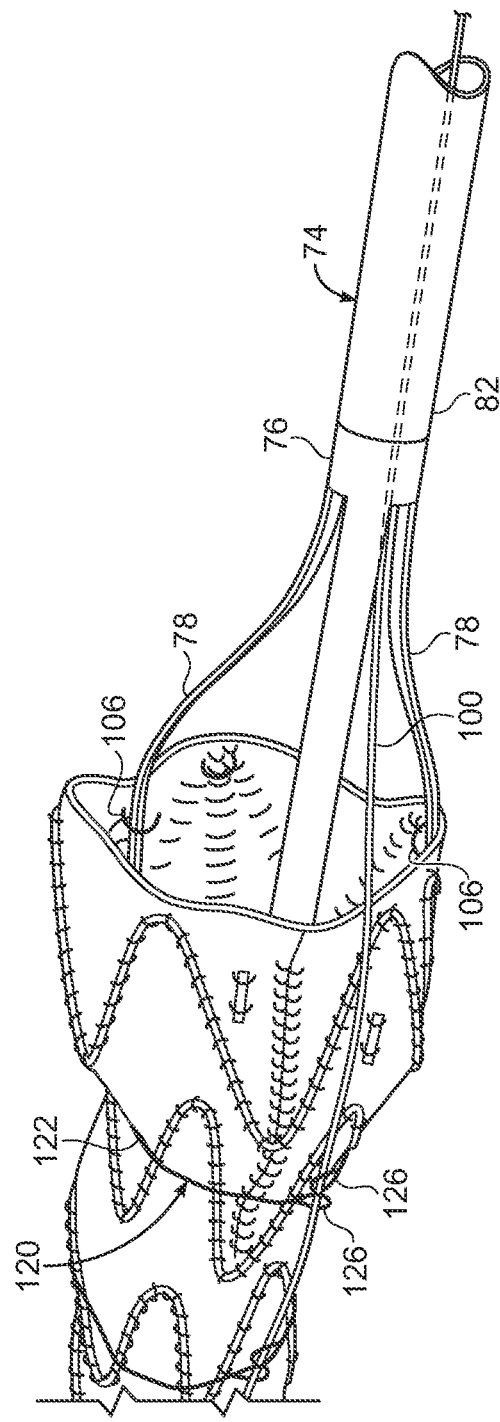
FIG. 18 is a three-dimensional representation of the torque component shown in FIG. 4, in combination with the distal end of a stent graft that has been partially deployed according to an embodiment of a method of the invention.

As can be seen in FIG. 18, radial constraint 120 radially constrains stent graft 38. In one embodiment, radial constraint 120 includes sutures 122, or threads, that span each of stents 48 of stent graft 38. Wire 100, extends through a loop 126 of each suture 122, whereby retraction of wire 100 from sutures 122 releases stent graft 38 from radial constraint 120. In an alternative embodiment, shown in FIG. 19, torque component 72A does not include hub. In this embodiment, arms can be fixed directly to pushrod 75 or can be fabricated by selective machining or cutting of a distal end of a rod to form arms 85 and pushrod 75. In still another embodiment (not shown), wire 100 is located on the interior of stent graft and extends through opening 94 through sutures 96 to the interior of the stent graft. As indicated from FIG. 11, in one embodiment, retraction of wire 100 will also release stent graft 38 from arm 78 of torque component 72. Alternatively, the radial constraint is flexible sheath 128 that extends between stent graft 38, and introducer sheath 18, and is tucked into, or under, nose cone 30, as shown in FIG. 20.

In one embodiment of a method of the invention, stent graft 38, which is in the first constrained state, as shown in FIG. 3, is directed to an aneurysm site of a subject. Introducer sheath 18 is then retracted by rotation of lead screw nut 32 about track 34 of handle body 12, as shown in FIG. 2, Option I, whereby abutment of lead screw nut 32 against distal handle 16 causes track 34 and introducer sheath 18, to which track 34 is attached, to move in proximal direction 11 relative to the surgeon. Alternatively, or subsequently, lead screw nut 32 can be pulled in proximal direction 11 by the surgeon to retract introducer sheath 18 in proximal direction 11 relative to guidewire catheter 24 and stent graft 38, as shown at FIG. 2 Option II. As can also be seen from FIG. 19, at least partial retraction of introducer sheath 18 in proximal direction 11 causes proximal end 40 of stent graft 38 to shift from a first constrained position, represented in FIGS. 3 and 18, to a second constrained position, which is maintained by radial constraint 120.

Figure 20:
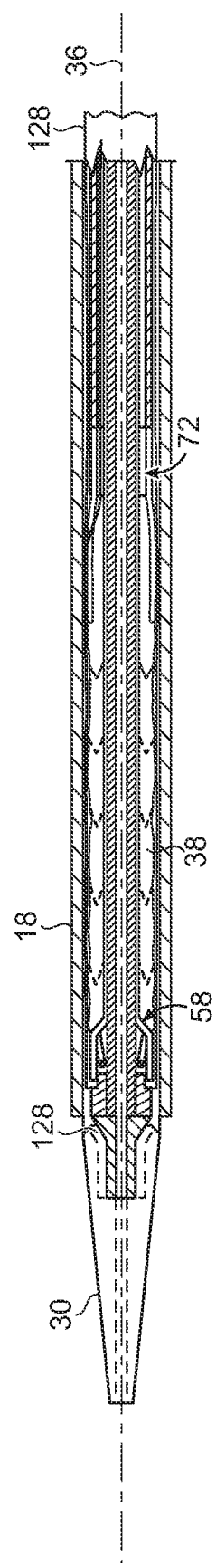
FIG. 20 is a cross-sectional representation of an alternative embodiment of a delivery system of the invention, further including a flexible sheath extending about the stent graft and within an introducer sheath.
Figure 21:
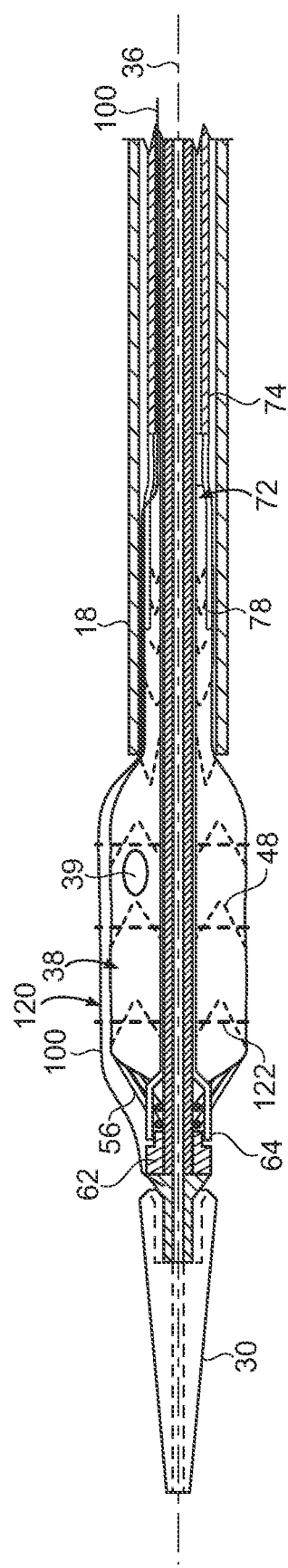
FIG. 21 is a cross-sectional view of the delivery system of the invention shown in FIG. 3, wherein the introducer sheath has been partially retracted from the stent graft.

As shown in FIG. 22, fully retracting introducer sheath 18 from stent graft 38 and from torque component 72 causes stent graft 38 to assume the second constrained position along its entire length, which is maintained by radial constraint 120. Also, shifting from the first constrained position to the second constrained position causes torque component 72 to radially expand from a first constrained position, shown in FIGS. 3, 20, and 21, to a second constrained position, shown in FIG. 22. Application of torque force to torque component 72, while the introducer sheath 18 is at least partially retracted, causes stent graft 38 to rotate about longitudinal axis 36.

Figure 23:
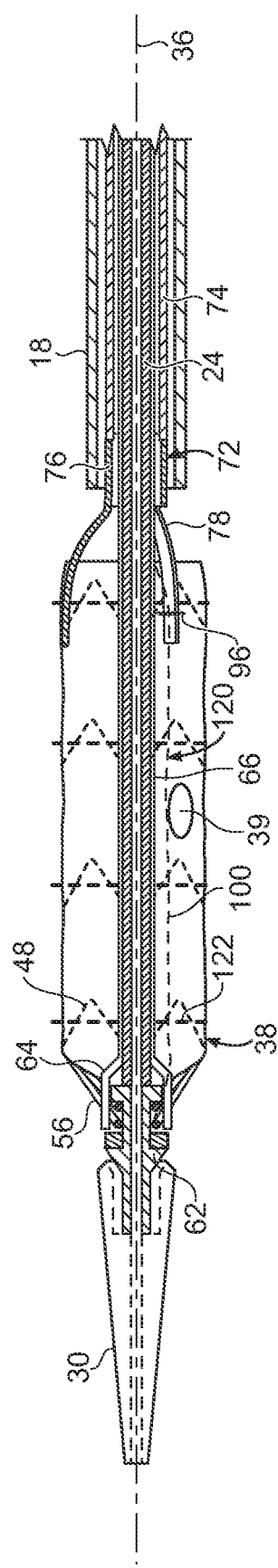
FIG. 23 is a cross-sectional view of the delivery system of the invention shown in FIG. 22, wherein the stent graft has been rotated about the guidewire catheter, and wherein a wire extending through a suture has been partially retracted from the sutures to partially release the stent graft.

For example, when stent graft 38 is in the second constrained position, shown in FIG. 22, torque component 72 can be rotated about guidewire catheter 24 by rotating proximal handle 14 (FIG. 2), which rotates pushrod 74 (FIG. 23), to which it is connected. This rotation of torque component 72 enables rotational alignment of at least one fenestration 39 of stent graft 38, as shown in the transition from FIG. 22 to FIG. 23. Stent graft 38 can also be longitudinally moved along longitudinal axis 36 (also referred to as axial movement) to properly position stent graft 38 at an aneurysm site. As noted above, suture 96, extending through arm 78, luminal graft component 44, and through which wire 100 extends, fixes distal end 42 of stent graft 38 to delivery system 10, thereby substantially preventing longitudinal collapse of stent graft 38 by friction between distal end 42 of stent graft 38 and an arterial wall during proximal movement (toward the clinician) of apex capture assembly 58, to which proximal end 40 is held in the captured state shown in FIG. 23.

Figure 24:
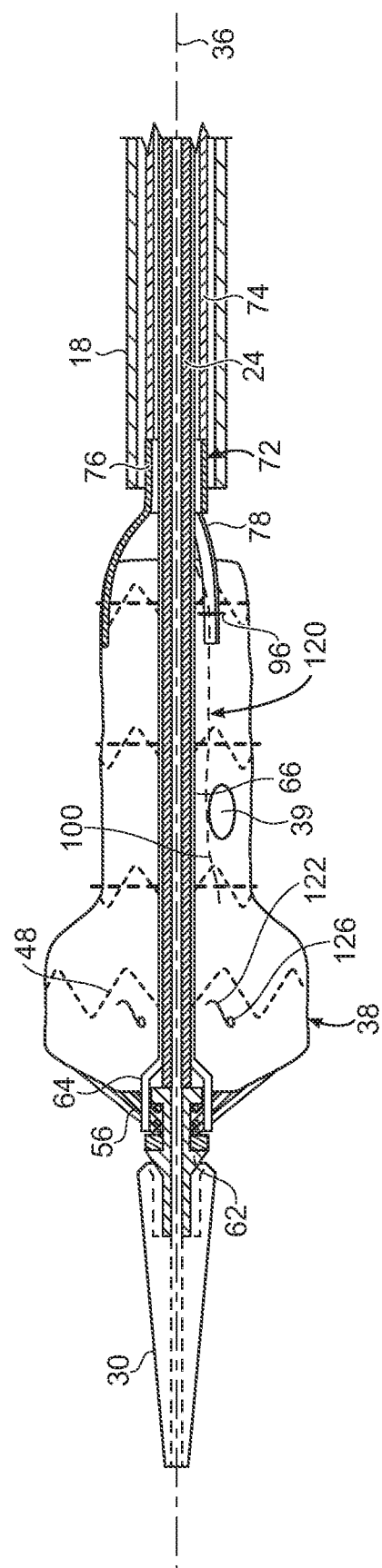
FIG. 24 is a cross-sectional view of the delivery system of the invention and stent graft shown in FIG. 23, wherein the wire has been completely retracted from the sutures, thereby fully releasing the stent graft.
Figure 25:
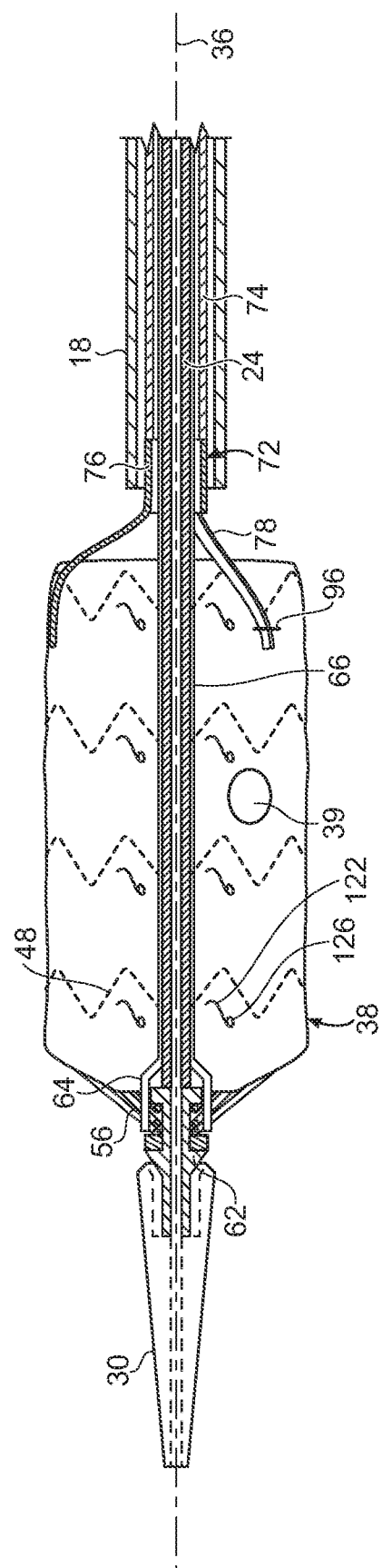
FIG. 25 is a cross-sectional view of the delivery system of the invention of the stent graft shown in FIG. 24, wherein the delivery system has been partially retracted from the fully deployed stent graft.
Figure 26:
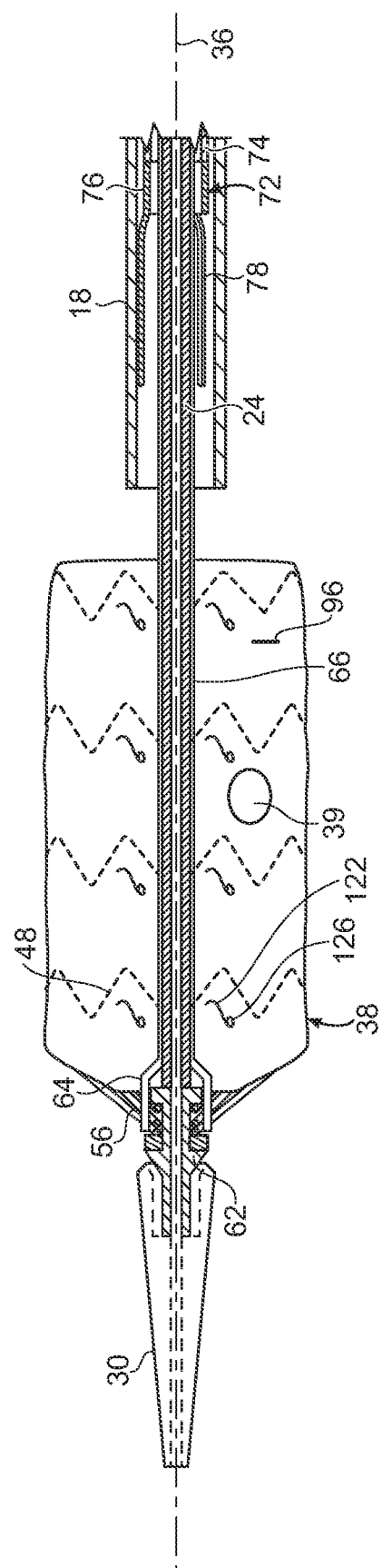
FIG. 26 is a cross-sectional view of the delivery system of the invention of the stent graft shown in FIG. 25, wherein the delivery system has been partially retracted from the fully deployed stent graft.
Figure 27:
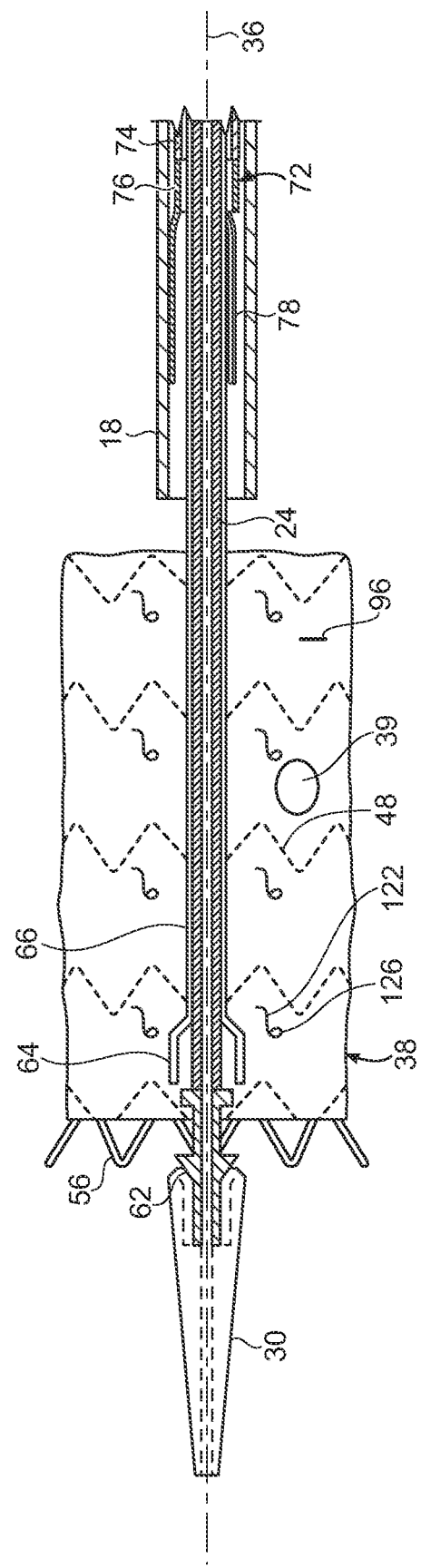
FIG. 27 is a cross-sectional view of the delivery system of FIG. 26, wherein the delivery system has been partially deployed from the fully deployed stent graft.
Figure 28:
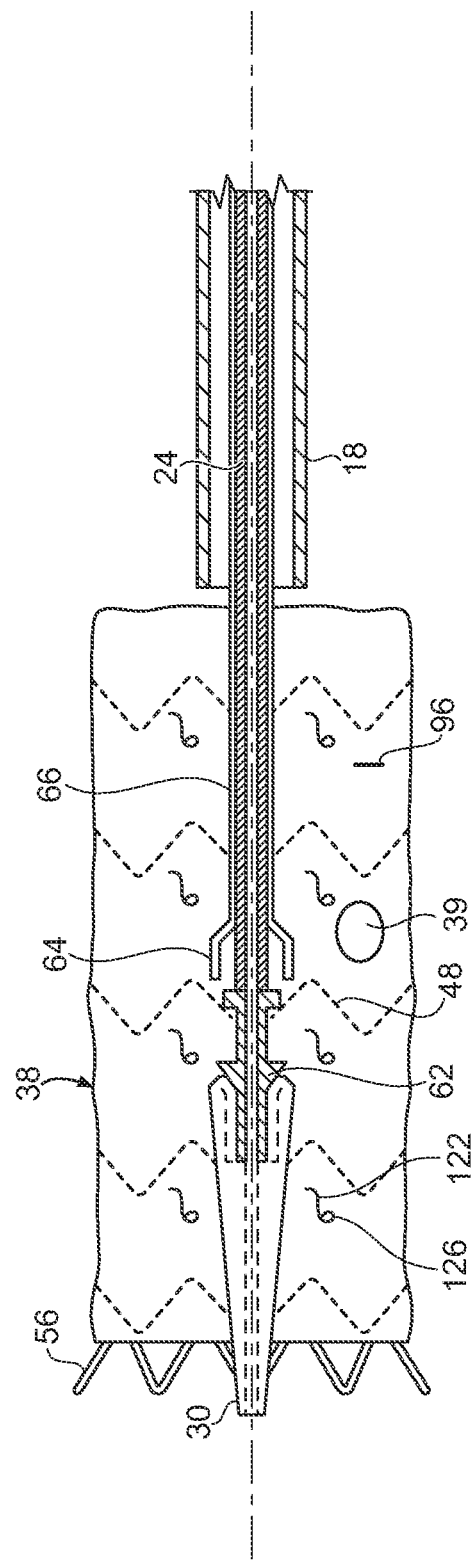
FIG. 28 is a cross-sectional view of the delivery system of FIG. 27, wherein the delivery system has been deployed from the fully deployed stent graft.

In the embodiment shown in FIG. 24, wire 100 of radial constraint 120 is retracted from sutures 122, thereby releasing sutures 122 of radial constraint 120 and allowing the remainder of stents 38 to fully expand in a radial direction and land at their proper locations without distortion of stent graft 38 or damage to the surgical site, as shown in FIG. 25. Thereafter, torque component 72 is retracted from distal end 42 of stent graft 38. Apex capture assembly 58 is then actuated by releasing apex capture catheter 66 from guidewire catheter 24 at proximal clasp assembly 68 (FIGS. 1 and 2), and retracting proximal apex capture component 64 and apex capture catheter 66, to which proximal apex capture component 64 is fixed, thereby releasing bare stent 56 from its captured state, shown in FIG. 26, to a released state, shown in FIG. 27. As a consequence of release, proximal end 40 of stent graft 38 will land at its designated location at the surgical site. As shown in FIG. 28, guidewire catheter 24 and apex capture catheter 66 can then be retracted from stent graft 38, and delivery device 10 can be removed from the subject, thereby completing the procedure.

It is to be understood that other delivery devices can be deployed to conduct the method of the invention. For example, stent graft 38 can be directed to an aneurysm site without the aid of an introducer sheath 18. In one such embodiment, stent graft 38 is introduced to a subject while being constrained only by radial constraint 120, without constraint by introducer sheath 18. In another embodiment, the method includes first directing the stent graft 38, while it is in a first constrained state and within introducer sheath 18, to a position distal to an aneurysm site, followed by advancement of the stent graft from the distal end 22 of the introducer sheath 18 to the aneurysm site.

In another embodiment, the radial constraint is the introducer sheath. For example, as shown in FIG. 29 as an exploded view, delivery system 150 of the invention for implanting a stent graft 152 (FIG. 29) includes proximal handle 154 and distal handle 156. Guidewire catheter 158 includes a proximal end 160 and distal end 162, and extends from distal handle 154. Nose cone 164 and apex capture device 157 are fixed at distal end 162 of guidewire catheter 158. Torque component 166 includes pushrod 168, and at least two arms 172, which can be self-expanding, extending from pushrod. Optionally, hub 170 is included as a link between pushrod 168 and arms 172. Hub 170 defines a lumen about longitudinal axis 176 and is fixed to pushrod 168. Arms 172 are disposed radially about hub 170 and extend distally from hub 170. The radial constraint, in this embodiment, is introducer sheath 174, which extends from distal handle 156.

FIG. 30A is an assembled view of delivery system 150 shown in FIG. 29. As can be seen in FIGS. 30A through 30C, each arm 172 is movable from a constrained state to an expanded state. In one embodiment, arms 172 of torque component 166 exhibit radial self-expansion away from longitudinal axis 176. Introducer sheath 174 extends longitudinally between hub 170 and distal end 162 of guidewire catheter 158 and radially constrains stent graft 152 extending distally from torque component 166 and about guidewire catheter 158. Application of torque force to arms 172 by rotation of torque component 166 about longitudinal axis 176 causes fenestration 180 of stent graft 152 to rotate about longitudinal axis 176 until it is rotationally aligned at the aneurysm site. In a method of the invention, advancement of the stent graft 152 within radial constraint 166 to an aneurysm site, followed by rotational alignment of at least one fenestration 180. Rotation of radial constraint 166 can be independent of any rotation of guidewire catheter 158 or proximal handle 154. Alternatively, rotation of radial constraint 166 can be in conjunction with rotation of guidewire catheter 158, such as by locking torque component 166 to proximal handle 154. Retraction of radial constraint 166 from stent graft 152 causes radial expansion of self-expanding arms 172 and self-expansion of stent graft 152 to thereby at least partially deploy stent graft 152. As shown in FIG. 30B, stent graft 152 is releasably secured to distal end 162 of guidewire catheter 158 at bare stent 159 by a suitable apex capture device 157, such as is known in the art. Bare stent 159 is released from guidewire catheter 158 by actuation of the apex capture device 157, and the remainder of delivery system 150 not implanted at the aneurysm is retracted from stent graft 152 and from the aneurysm site as shown in FIG. 30C.

In another embodiment, shown in FIG. 31A, stent graft delivery system 198, which is an alternate embodiment from that shown in FIG. 18, includes circular ligatures 200 extending about the periphery of stent graft 38 to form diametrically opposed ends 127,129 of circular ligatures 200 that are linked by wire 46. Wire 100 is stabilized by anchor loops 202,204. FIG. 31B is a detail of the circular ligature 200 shown in FIG. 31A, configured as a circle when not wrapped about stent graft 28. FIG. 31C is a detail of circular ligature 200 when configured to be wrapped about stent graft 28. As can be seen from FIGS. 31A-31C, diametrically opposed ends 127,129 of circular ligature 200 secure circular ligature 200 about stent graft 28 when they are linked by wire 100.

Figure 19:
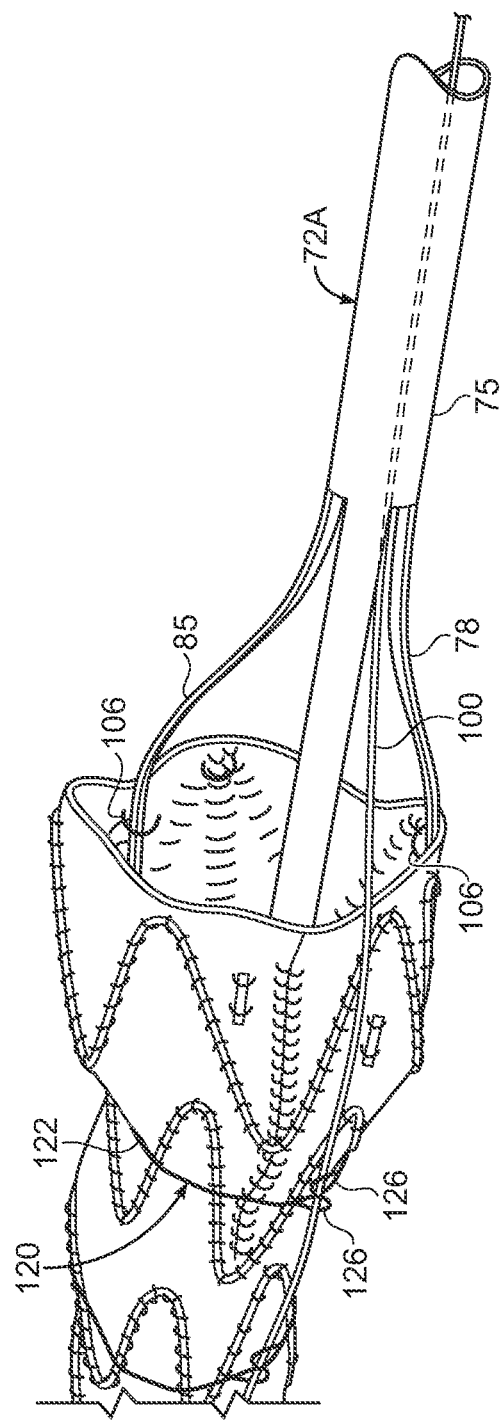
FIG. 19 is a three-dimensional representation of the torque component shown in FIG. 6, in combination with a distal end of a stent graft that has been partially deployed according to an embodiment of the invention.
Figure 32A:
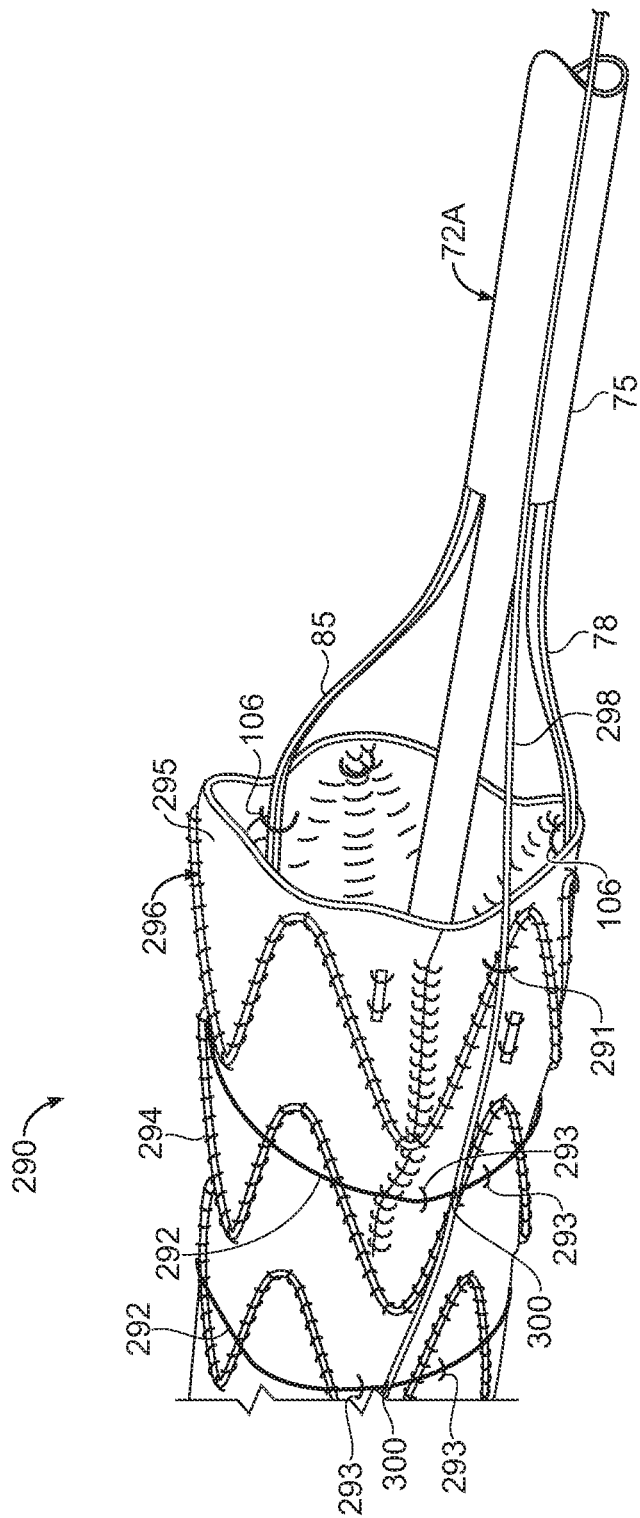
FIG. 32A is a perspective view of still another embodiment of the invention, wherein the wire of the stent graft delivery system of FIG. 19 is replaced with a notched control rod, wherein the ligature traverses the notch, whereby rotation of the control rod about its longitudinal axis causes the ligature to wrap about the control rod, thereby radially constricting the stent graft.
Figure 32B:
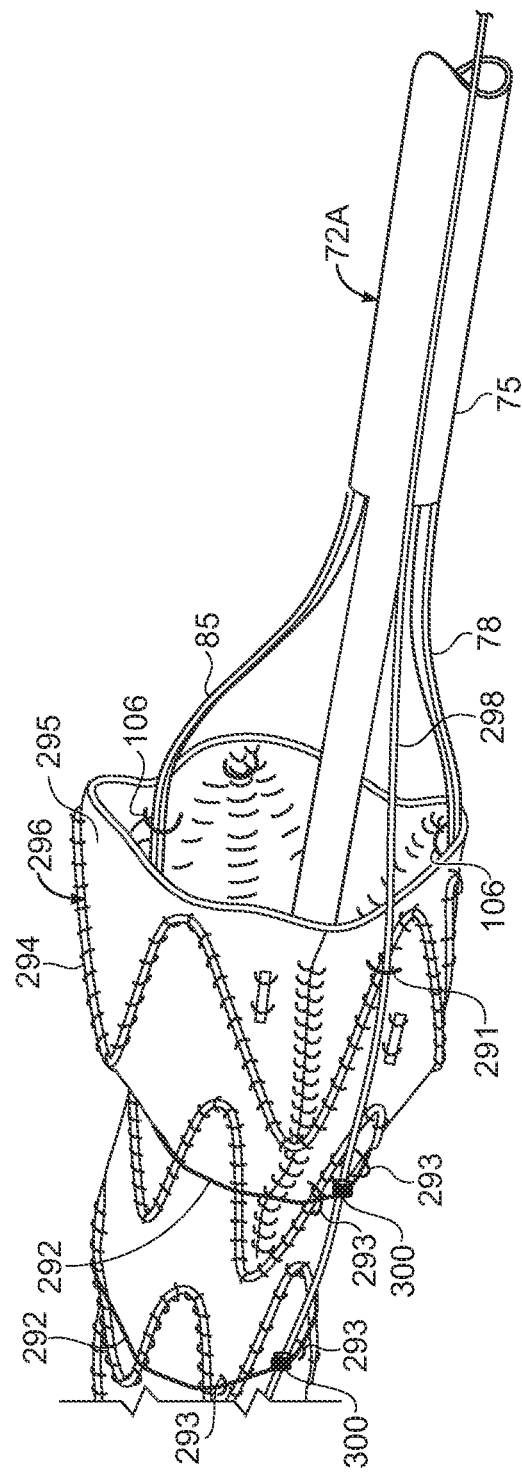
FIG. 32B is a perspective view of the embodiment of the invention shown in FIG. 32A, but wherein the stent graft has been radially constricted by rotation of the control rod to thereby wrap the ligature about the control rod.

Another embodiment of a stent graft delivery system of the invention is shown in FIG. 32A, which is an alternate embodiment from that shown in FIG. 19. As shown in FIG. 32A, stent graft delivery system 290 includes a plurality of ligatures 292 that extend about the perimeter of stents 294 at stent graft 296, and are releasably secured to control rod 298 by notch 300, whereby rotation of control rod 298 causes uniform constriction of respective stents 294 of stent graft 296. In a method of the invention, represented by the transition from FIG. 32A to FIG. 32B axially rotating control rod 298 causes ligatures 292 to wrap around control rod 298, thereby radially constricting stents 294 traversed by ligatures 92 linked to control rod 298 at notch 300. Optionally, at least one loop 291 secures control rod 298 to luminal graft component 295 of stent graft 296. In a further embodiment, at least one loop 293 secures ligatures 292 to luminal graft component 295.

FIG. 33 is an exploded view of another embodiment of a control rod of a stent graft delivery system of the invention. As shown in FIG. 33, control rod 370 includes outer tube 372 defining outer tube fenestration 374. Inner tube 376 defines inner tube fenestration 378. Inner tube 376 has a diameter smaller than that of an inside diameter of outer tube 372. Wire 380 has a diameter smaller than an interior diameter of inner tube 376. When assembled, as shown in FIG. 34, wire 380 extends longitudinally through the inner tube 376, and inner tube 376 extends longitudinally within outer tube 372. Inner tube fenestration 378 is aligned with outer tube fenestration 374, and wire 380 traverses both inner tube fenestration 378 and outer tube fenestration 374.

FIG. 35A is a side view of a detail of a stent graft delivery system of the invention, wherein control rod 370 of FIGS. 33 and 34 extends longitudinally along stent graft 382 at outside surface 384. Ligature 386 is threaded between wire 380 and an inside surface of inner tube 376 while inner tube fenestration 378 and outer tube fenestration 374 are aligned. Stent 388, including struts 389, of stent graft 382 can be radially constricted by retracting in the direction of arrow 373, inner tube 376 within outer tube 372, thereby causing ligature 386 to be drawn within outer tube 372, as can be seen in the transition from FIG. 35A to FIG. 35B. In an embodiment, such as wherein ligature 386 extends radially over struts 389 on either side of control rod 370, ligature 386 can be stabilized, at least in part, by at least one ligature suture 387 spanning ligature 386. In one embodiment, control rod 372 is stabilized at stent graft 382 by control rod suture 385.

In another embodiment of a method of the invention, shown in the transition from FIG. 35A to FIG. 35C, rather than retracting inner tube 376 and wire 362 within outer tube 372, ligature 386, is radially constricted by axially rotating inner tube 376 relative to outer tube 372 to thereby wrap ligature 386 about inner tube 376, radially constricting stent 388, struts 389 of which are traversed by ligature 386.

Figure 36A:
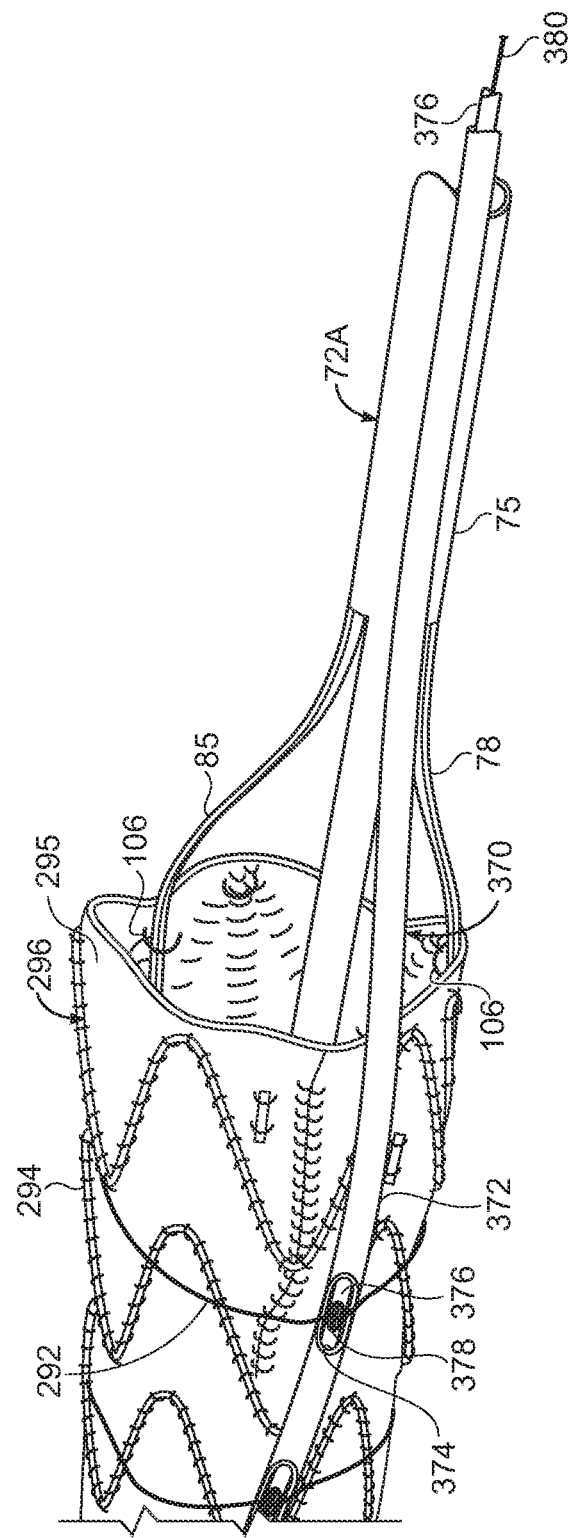
FIG. 36A is another embodiment of the invention, like that shown in FIG. 32A, but wherein the control rod is that shown in FIGS. 33 and 34.
Figure 36B:
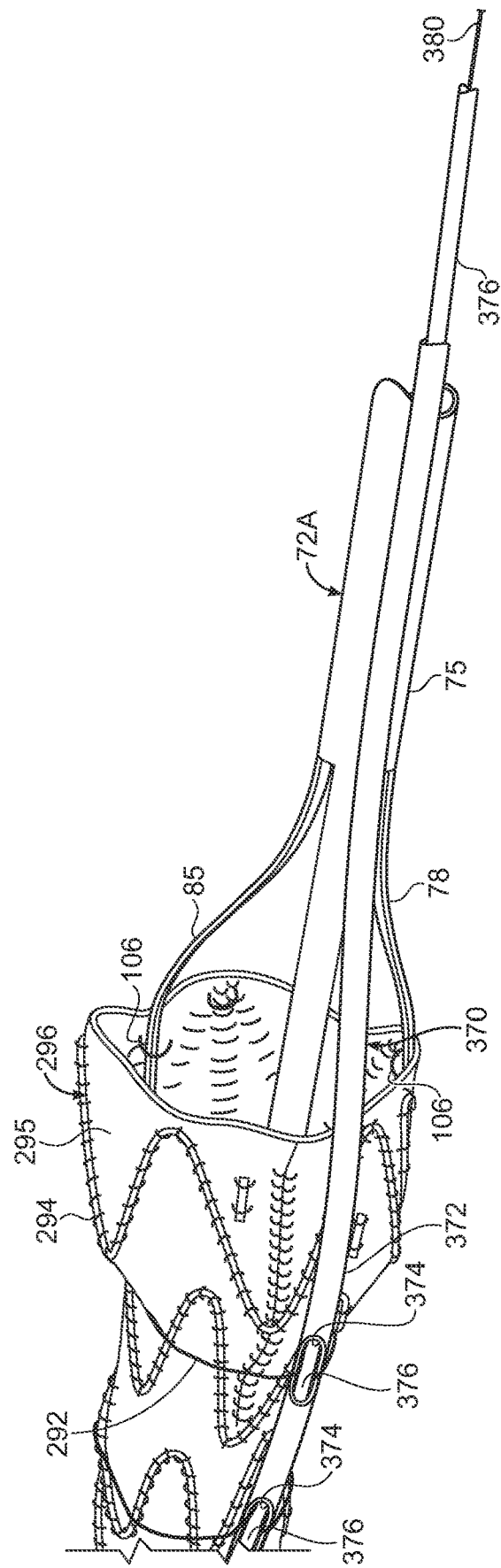
FIG. 36B is a perspective view of the embodiment shown in FIG. 36A, but wherein the ligature about the stent graft has been radially constricted by proximally moving the inner tube relative to the outer tube and relative to the stent graft, thereby drawing a portion of the ligature into the outer tube.

FIG. 36A is another embodiment of the invention, like that shown in FIG. 32A, but wherein control rod 270 is that shown in FIGS. 33 and 34. FIG. 36B is a perspective view of the embodiment shown in FIG. 36A, but wherein ligature 292 about stent graft 296 has been radially constricted by proximally moving inner tube 376 relative to the outer tube 372 and relative to stent graft 296, thereby drawing a portion of ligature 292 into outer tube 372.

FIG. 37 is an exploded side view of another embodiment of the stent graft delivery system of the invention. As shown therein, stent graft delivery system 410 includes guidewire catheter 412 having proximal end 414 and distal end 416. Proximal handle 418 is fixed to proximal end 414 of guidewire catheter 412. Nose cone 420 and apex capture device 421 are fixed to distal end 416 of guidewire catheter 412. Torque component 466 includes pushrod 468, and at least two arms 472, which can be self-expanding, extending from pushrod 468. Optionally, hub 470 is included as a link between pushrod 468 and arms 472. Hub 470 defines a lumen about longitudinal axis 476 and is fixed to pushrod 468. Arms 472 are disposed radially about hub 470 and extend distally from hub 470. Torque component handle 467 is at a proximal end of pushrod 468. Wire 422 includes proximal end 424 and distal end 426. Wire 422 can be fabricated of a suitable material, such as is known in the art, including, for example, Nitinol or some other shape memory alloy. Wire 422 is sufficiently flexible not to injure the patient during advancement to an aortic aneurysm of a patient. Wire handle 428 is fixed at proximal end 424 of wire 422. Introducer sheath 430 includes proximal end 432 and distal end 434, and distal handle 436 is fixed to proximal end 432 of introducer sheath 430. Stent graft 438 includes proximal end 440, distal end 442, luminal graft component 444, stents 446 distributed along luminal graft component 444, and ligatures 448, arranged and configured as discussed above. Bare stent 449 is fixed to distal end of stent graft 438.

FIG. 38A is an assembled side view of stent graft delivery system 410 shown in FIG. 37, wherein stent graft 438 has been loaded within distal end 434 of introducer sheath 430, and radially constricted, at least in part, by wire 422 threaded through diametrically opposed ends 150 of circular ligatures 448, as discussed above, and through stabilizing anchor loops 453. In an embodiment, stent graft 438 includes fenestration 439.

In a method of the invention, stent graft delivery system 410 is advanced to arterial aneurysm 452 of a patient. In one embodiment, shown in FIG. 38A, introducer sheath 430 is advanced to aneurysm site 452 to thereby place stent graft 438 at aneurysm 452. As can be seen in FIG. 38B, distal handle 436 is retracted in a proximal direction indicated by arrow 460 toward proximal handle 418, thereby retracting introducer sheath 430 from stent graft 438 at aneurysm 452. As can be seen in FIG. 38B, despite retraction of introducer sheath 430, stent graft 438 is maintained in a radially constricted position by wire 422 extending through ligature loops 450 of ligatures 448 traversing struts of stents 446 distributed longitudinally along stent graft 438. It is to be understood, however, that in an alternative embodiment, where wire 422 is sufficiently rigid, stent graft delivery system 410 can be advanced within an artery to a position distal to arterial aneurysm 452, wherein stent graft 438 is directed to arterial aneurysm 452 by advancement of proximal handle 418 and wire handle 428 in a distal direction indicated by arrow 462 toward distal handle 436 to thereby direct radially constricted stent graft 418 from introducer sheath 430 to arterial aneurysm 452.

Application of torque force to arms 472 by rotation of torque component 466 about longitudinal axis 476 causes fenestration of stent graft 452 to rotate about longitudinal axis 476 until it is rotationally aligned at the aneurysm site. In a method of the invention, advancement of the stent graft 452 within radial constraint 466 to aneurysm 452, is followed by rotational alignment of at least one fenestration 480.

Following direction of stent graft to a position that spans aneurysm 452 and at least partial rotational and axial alignment of stent graft at aneurysm 452, wire 422 is retracted from loops 450 of ligatures and from anchor loops 453. Proximal retraction of wire handle 428 toward proximal handle 418, in the direction indicated by arrow 460, withdraws wire 422 from suture loops 450 of ligatures 448 and anchor loops 453, thereby enabling stent graft 438 to fully expand from its radially constricted state, shown in FIG. 38B, to a radially expanded state, shown in FIG. 38C. As shown in FIG. 38D, stent graft 452 is releasably secured to distal end 462 of guidewire catheter 458 at bare stent 459 by a suitable apex capture device 457, such as is known in the art. Bare stent 459 is released from guidewire catheter 458 by actuation of the apex capture device 457. Thereafter, stent graft 438 is fully implanted within aneurysm, and the remainder of stent graft delivery device 410 is retracted from stent graft 438 and the patient, as shown in FIG. 10E, thereby completing treatment of aneurysm 452 of the patient by the method of the invention.

FIG. 39 is an exploded view of another embodiment of a stent graft delivery system of the invention. As shown therein, stent graft delivery system 520 includes guidewire catheter 522 having proximal end 524 and distal end 526. Proximal handle 528 is fixed to proximal end 524 of guidewire catheter 522. Nose cone 530 and apex capture device 531 are fixed to distal end 526 of guidewire catheter 522. Control rod 532 includes proximal end 534 and distal end 536. Control rod handle 538 is fixed to proximal end 534 of control rod 532. Torque component 566 includes pushrod 568, and at least two arms 572, which can be self-expanding, extending from pushrod 568. Optionally, hub 570 is included as a link between pushrod 568 and arms 572. Hub 570 defines a lumen about longitudinal axis 576 and is fixed to pushrod 568. Arms 572 are disposed radially about hub 570 and extend distally from hub 570. Torque component handle 567 is at a proximal end of pushrod 568. Control rod 532 includes notch 533. Stent graft 540 includes luminal graft component 542 and stents 544. Stents 544 include struts 546 that define proximal and distal apices. Ligature 548 traverses struts 546 of stents 544. Introducer sheath 550 includes proximal end 552 and distal end 554. Distal handle 556 is fixed to proximal end 552 of introducer sheath 550.

FIG. 40A is a side view of the stent graft of the delivery system shown in FIG. 39, but when assembled, and wherein a stent graft 540 has been loaded within distal end 554 of introducer sheath 550. In an embodiment, stent graft 540 includes bare stent 521 at proximal open end 552 having proximal apices and distal apices that, optionally, include barbs.

FIG. 40B is a side view of a stent graft delivery system of FIGS. 39 and 40A, following direction of stent graft delivery system 520 to arterial aneurysm 558 of a patient, such as an aortic aneurysm, and location of stent graft 540 of stent graft delivery system 520 at a position spanning aneurysm site 558. Application of torque force to arms 572 by rotation of torque component 566 about longitudinal axis 576 causes fenestration of stent graft 552 to rotate about longitudinal axis 576 until it is rotationally aligned at the aneurysm site. In a method of the invention, advancement of the stent graft 562 within radial constraint 466 to aneurysm 452, is followed by rotational alignment of at least one fenestration 580. As further shown in FIG. 40B, according to a method of the invention, stent graft 540 is located at arterial aneurysm 558, such as is shown in the transition between FIGS. 40A and 40B, and at least one stent 544 is radially constricted by ligature 548, which is wrapped about control rod 532 while stent graft 540 is positioned at arterial aneurysm 558 by the surgeon in the direction indicated by arrow 570. In the embodiment shown in FIG. 40B, stent graft 540 is exposed to aneurysm 558 by retraction of distal handle 556 toward proximal handle 528 by the surgeon in the direction indicated by arrow 570. It is to be understood, however, that, alternatively, stent graft 540 can be advanced from within introducer sheath 550 at distal end 559 to arterial aneurysm 558 by advancing proximal handle 528 and control rod 532 toward distal handle 556 in the direction of arrow 572. In either case, the length of the portion of ligature 548 traversing stent 544 can be increased or decreased controllable by axial rotation of control rod handle 538 and consequent rotation of control rod 532 by the surgeon during positioning of stent graft 540 at aneurysm 558. In one embodiment, stent graft 540 is positioned so that fenestration 564 at stent graft 540 is properly aligned with arterial branch 560 for subsequent placement of branch prosthesis 562 through fenestration 564 to arterial branch 560.

Upon completion of positioning of stent graft at aneurysm site 558, ligature 548 is released from control rod 532. Depending upon the embodiment of the control rod 532, as discussed above, for example, ligature 548 can be released from control rod 532 by proximally retracting control rod 532, as shown in the transition from FIG. 40B to FIG. 40C, or, by other means, such as by proximal retraction of a wire within a tube, as described above with reference to the embodiments of FIGS. 33-36B, thereby releasing ligature 548. As shown in FIG. 38D, stent graft 540 is releasably secured to distal end 526 of guidewire catheter 522 at bare stent 521 by a suitable apex capture device 531, such as is known in the art. Bare stent 521 is released from guidewire catheter 522 by actuation of apex capture device 531, and the remainder of delivery system 520 not implanted at aneurysm 558 is retracted from stent graft 540 and from aneurysm 558. Deployment of stent graft 540 then is complete.

Figure 41:
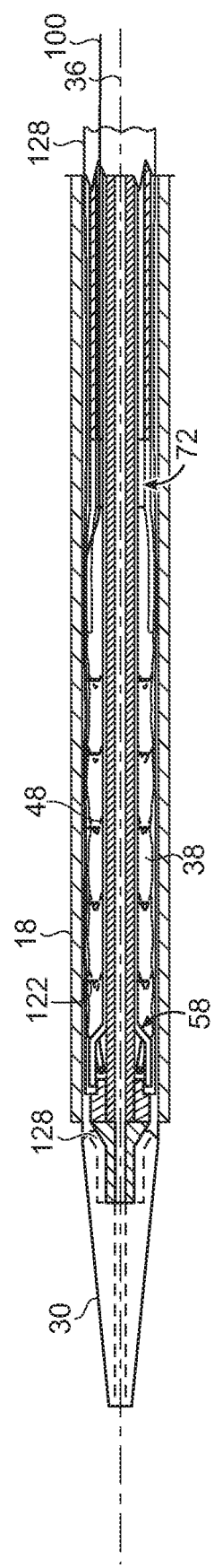
FIG. 41 is a cross-section of another embodiment of a stent graft delivery system of the invention, wherein a stent graft is radially constricted by a two-stage radial release component that includes a flexible sheath and a wire linking ends of radially constricting sutures.
Figure 42:
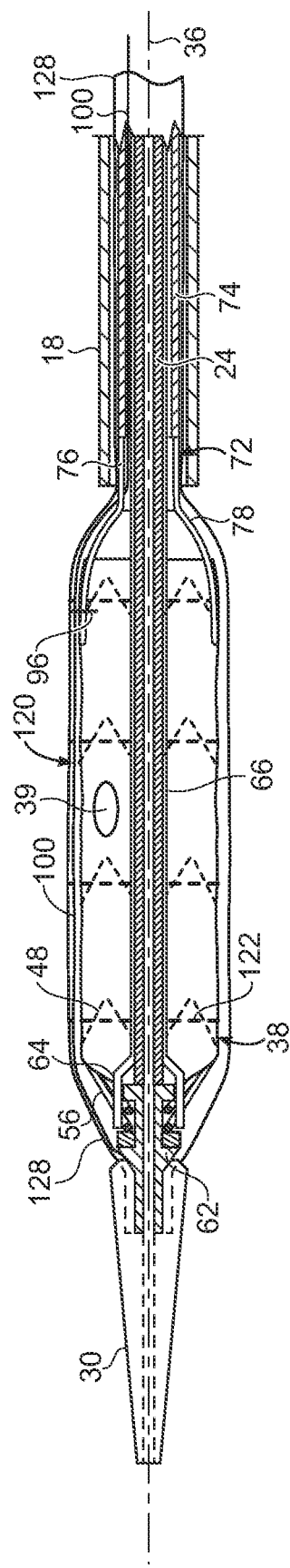
FIG. 42 is a cross-section of the embodiment shown in FIG. 41 following proximal retraction of an introducer sheath and before actuation of the two-stage radial release component.

In another embodiment of the stent graft delivery system of the invention, shown in FIGS. 41 and 42, the delivery system is like that shown in FIGS. 20 and 22, described above, but with constricting sutures 122 and wire 100 in addition to sheath 128. In this embodiment, radial constraint 120 includes sutures 122, wire 100, and flexible sheath 128. Sutures 122, or threads, span each of stents 48 of stent graft 38. Wire 100, extends through a loop 126 of each suture 122, whereby retraction of wire 100 from sutures 122 releases stent graft 38. Flexible sheath 128 extends between stent graft 38, and introducer sheath 18, and its tucked into, or under, nose cone 30. FIG. 42 shows the stent graft delivery system of FIG. 41, but following retraction of introducer sheath 18, thereby causing flexible sheath 128 to radially constrict stent graft 120. A two stage expansion of stent graft 120 is thereby possible, whereby proximal retraction of flexible sheath 128 from stent graft 120 and subsequent partial radial expansion of stent graft 120 is a first stage, and proximal retraction of wire 100 from sutures 122 thereafter allows full radial expansion of stent graft 120 (but for release of bare stent 56), constituting a second stage.

Although not shown, it is to be understood that control rods can be employed in the device and method of the invention to independently radially constrict various longitudinal portions of a stent graft, such as proximal and distal portions of a stent graft. It is also to be understood that a plurality of control rods can be distributed radially about a stent graft, either evenly, evenly in conjunction with a fenestration in the stent graft, or in another pattern or unevenly. It is also to be understood that the stent graft delivery system of the invention can include a plurality of control rods that each separately and independently control radial expansion of the same portion of stents, in particular a proximal portion of stents. The plurality of control rods are laterally and longitudinally arranged relative to each other about a circumference of the outside or inside surface of the luminal graft component (not shown).

The teachings of all patents, published applications and references cited herein are incorporated by reference in their entirety. The relevant teachings of all patents, published applications and references cited herein are incorporated by reference in their entirety. The relevant teachings of U.S. Pat. Nos. 8,292,943; 7,763,063; 8,308,790; 8,070,790; 8,740,963; 8,007,605; 9,320,631; 8,062,349; 9,198,786; 8,062,345; 9,561,124; 9,173,755; 8,449,595; 8,636,788; 9,333,104; 9,408,734; 9,408,735; 8,500,792; 9,220,617; 9,364,314; 9,101,506; 8,998,970; 9,554,929; 9,439,751; 9,592,112; 9,655,712, 9,827,123, 9,877,857, 9,907,686; U.S. patent application Ser. Nos. 14/575,673; 15/166,818; 15/167,055; 14/272,818; 14/861,479; 15/478,424; 15/478, 737; 15/587,664; 15/604,032; 15/672,404; 15/816,772; 15/839,272; 15/417,467; PCT/US2017/025844; PCT/US2017/025849; PCT/US2017/025912; PCT/US2017/034223; PCT/US2017/046062; PCT/US2018/019355; PCT/US2018/019344; PCT/US2018/019349; PCT/US2018/019353; PCT/US2018/019354; PCT/US2018/019352; PCT/US2018/019342; PCT/US2018/019350; PCT/US2018/019356; and PCT/US2018/019351 are also incorporated by reference in their entirety.

While example embodiments have been particularly shown and described, it will be understood by those skilled in the art that various changes in form and details may be made therein without departing from the scope of the embodiments encompassed by the appended claims. For example, although not shown, the at least one fenestration of the stent grafts employed in the methods or as components of the delivery systems of the invention can include fenestration locks as described in PCT/US2018/019352; moveable fenestrations as described in PCT/US2018/019353; fenestration rings as described in PCT/US2018/019351; and crimped adapters as described in PCT/US2018/019350, the relevant teachings of all of which are hereby incorporated by reference in their entirety. Also for example, although not shown, a flexible sheath for use in the delivery systems of the invention can include an arrangement of openings that will cause the flexible sheath to have a luminal configuration having a constricted diameter and a ligature extending through the openings that causes the openings to conform to the arrangement, thereby configuring the flexible sheath to confirm to the constricted radial diameter of the luminal configuration, the ligature being proximally retractable from the openings to thereby release the flexible sheath from the constricted radial diameter, as described in PCT/US2018/019354, the relevant teachings of which are hereby incorporated by reference in their entirety.

What is claimed is:

1. A delivery system for implanting a stent graft, comprising:
    a) a longitudinal body defining a longitudinal axis and having a proximal handle and a distal handle;
    b) a guidewire catheter having a proximal end and a distal end, and extending from the distal handle of the longitudinal body;
    c) a stent graft defining an opening and extending about the guidewire catheter, the stent graft including
        i) a luminal graft component, and
        ii) a plurality of radial stents distributed longitudinally along the luminal graft component, at least one of the stents having struts that are joined to define proximal and distal apices;
    d) a radial constraint at the stent graft extending about the guidewire catheter;
    e) a torque component, including
        i) a pushrod extending about the guidewire catheter and distally from the proximal handle,
        ii) at least two arms disposed radially about and extending distally from the pushrod, each arm being moveable from a constricted state to an expanded state, whereby the torque component exhibits radial expansion, and whereby application of torque force to the torque component by rotation of the proximal handle about the longitudinal axis causes the stent graft to rotate about the longitudinal axis, wherein at least one of the arms defines an opening at a distal end,
        iii) a suture ring secured to the arm at the opening defined by the at least one arm and extending through the opening defined by the stent graft, and extending from the opening defined by the stent graft, and
        iv) a wire extending from the longitudinal body and through the suture to secure the stent graft to the at least one arm, whereby retraction of the wire toward the handle releases the stent graft from the at least one arm.

2. The delivery system of claim 1, further including a hub linking the pushrod to the at least two arms.

3. The delivery system of claim 2, wherein at least a portion of the arms are articulated.

4. The delivery system of claim 1, wherein the arms are self-expanding from the constricted state to the expanded state.

5. The delivery system of claim 1, wherein each of the at least two arms, when viewed at an angle normal to the longitudinal axis of the longitudinal body, has a curvilinear shape in the expanded state.

6. The delivery system of claim 1, wherein the radial constraint includes at least one of a thread and wire combination, and a flexible sheath extending about the stent graft, whereby the stent graft can be released from constraint by withdrawing the wire from the thread or the flexible sheath from the stent graft.

7. The delivery system of claim 6, wherein the radial constraint includes both the thread and wire combination, and the flexible sheath extending about the stent graft, whereby the stent graft can be released from constraint by removing the flexible sheath in one stage, and the wire can be withdrawn from the thread in another stage.

8. The delivery system of claim 1, further including an apex capture catheter extending distally from the distal end of the longitudinal body and about the guidewire catheter, the apex capture catheter being moveable between a first position and a second position, and an apex capture device having a distal capture component at a distal end of the catheter, and a proximal capture component at a distal end of the apex capture catheter, wherein the distal capture component and the proximal capture component together define an interior space that captures a proximal stent of the stent graft when the apex capture catheter is in the second position.

9. The delivery system of claim 1, wherein the radial constraint includes an introducer sheath extending about and radially constricting the torque component and the stent graft, the introducer sheath extending distally from the longitudinally body and being retractable from the stent graft and at least a portion of the torque component by at least one of retraction of the introducer sheath and advancement of the pushrod and guidewire catheter.

10. The delivery system of claim 1, further including a nose cone at the distal end of the guidewire catheter.

11. The delivery system of claim 1, wherein each arm has a cross section that has radial height less than a width at the cross section along at least a portion of a length of the at least one arm.

12. The delivery system of claim 1, wherein two arms are fixed to a distal end of the pushrod at a proximal end of each arm.

13. The delivery system of claim 12, wherein each of the two arms are evenly spaced relative to each other about the longitudinal axis of the pushrod.

14. The delivery system of claim 1, wherein three arms are fixed to a distal end of the pushrod at a proximal end of each arm.

15. The delivery system of claim 14, wherein each of the three arms are evenly spaced relative to each other about the longitudinal axis of the pushrod.

16. The delivery system of claim 1, wherein the at least two arms includes four arms are fixed to the distal end of the hub at the proximal end of each arm.

17. The delivery system of claim 16, wherein each of the four arms are evenly spaced relative to each other about the longitudinal axis of the longitudinal body.

18. A delivery system for implanting a stent graft, comprising:
    a) a longitudinal body defining a longitudinal axis and having a proximal handle and a distal handle;
    b) a guidewire catheter having a proximal end and a distal end, and extending from the distal handle of the longitudinal body;
    c) a stent graft extending about the guidewire catheter, the stent graft including
        i) a luminal graft component,
        ii) a proximal end and a distal end, iii) a plurality of radial stents distributed longitudinally along the luminal graft component, at least one of the stents having struts that are joined to define proximal and distal apices, and iv) a suture;

d) a radial constraint at the stent graft extending about the guidewire catheter and radially constraining the stent graft;

e) a torque component, including i) a pushrod extending about the guidewire catheter and distally from the proximal handle, and ii) at least two arms disposed radially about and extending distally from the pushrod, each arm being moveable from a constricted state to an expanded state, whereby the torque component exhibits radial expansion, and whereby application of torque force to the torque component by rotation of the proximal handle about the longitudinal axis causes the stent graft to rotate about the longitudinal axis, wherein the distal end of the stent graft extends about the at least two arms, and wherein the suture secures at least a portion of the arms from rotational movement relative to the stent graft, whereby the torque component is substantially prevented from rotating within the stent graft before deployment.

19. The delivery system of claim 1, wherein the at least two arms each independently have a length in a range of between about one inch and about five inches.

20. The delivery system of claim 1, wherein the arms of the torque component extend outside the stent graft.

21. A delivery system for implanting a stent graft, comprising:

a) a longitudinal body defining a longitudinal axis and having a proximal handle and a distal handle;

b) a guidewire catheter having a proximal end and a distal end, and extending from the distal handle of the longitudinal body;

c) a stent graft extending about the guidewire catheter, the stent graft defining an opening and including i) a luminal graft component, and ii) a plurality of radial stents distributed longitudinally along the luminal graft component, at least one of the stents having struts that are joined to define proximal and distal apices;

d) a radial constraint at the stent graft extending about the guidewire catheter;

e) a torque component, including i) a pushrod extending about the guidewire catheter and distally from the proximal handle, and ii) at least two arms disposed radially about and extending distally from the pushrod, each arm being moveable from a constricted state to an expanded state, whereby the torque component exhibits radial expansion, and whereby application of torque force to the torque component by rotation of the proximal handle about the longitudinal axis causes the stent graft to rotate about the longitudinal axis, wherein the at least one of the arms of the torque component extends through the opening.

22. The delivery system of claim 21, wherein the at least one of the arms of the torque component extends distally from inside the stent graft through the opening to outside the stent graft.

23. The delivery system of claim 22, wherein at least one of the arms of the torque component extends distally from outside the stent graft through the opening to inside the stent graft.

24. The delivery system of claim 23, wherein at least one of the arms of the torque component extend distally through two openings in the stent graft.

25. The delivery system of claim 21, wherein the stent graft includes at least one stent component secured within the graft component of the stent graft, and wherein at least one of the arms of the torque component extends between the stent component and the graft component.

26. The delivery system of claim 21, wherein at least one stent component is secured outside the graft component and wherein at least one of the arms of the torque component extends between the stent component and the graft component.

27. A delivery system for implanting a stent graft, comprising:

a) a longitudinal body defining a longitudinal axis and having a proximal handle and a distal handle and a handle body extending from the proximal handle to the distal handle;

b) a guidewire catheter having a proximal end and a distal end, and extending from the distal handle of the longitudinal body;

c) a stent graft extending about the guidewire catheter, the stent graft including i) a luminal graft component, and ii) a plurality of radial stents distributed longitudinally along the luminal graft component, at least one of the stents having struts that are joined to define proximal and distal apices;

d) a radial constraint at the stent graft extending about the guidewire catheter;

e) a torque component, including i) a pushrod extending about the guidewire catheter and distally from the proximal handle, and ii) at least two arms disposed radially about and extending distally from the pushrod, each arm being moveable from a constricted state to an expanded state, whereby the torque component exhibits radial expansion, and whereby application of torque force to the torque component by rotation of the proximal handle about the longitudinal axis causes the stent graft to rotate about the longitudinal axis, wherein the proximal handle is fixed to the pushrod and can rotate about the handle body to thereby rotate the torque component.

28. The delivery system of claim 27, further including a track at the longitudinal body, and an introducer sheath extending about and constraining the torque component and the stent graft, the introducer sheath extending distally from the track being retractable from the stent graft and the torque component by retraction of the introducer sheath, and a lead screw nut extending about the handle body and threadably engaged with the track, whereby the track and the introducer sheath can be retracted by rotation of the lead screw nut about the longitudinal body, or by retraction of the lead screw nut longitudinally along the handle body.

* * * * *